US010561563B2

(12) United States Patent
Herr et al.

(10) Patent No.: US 10,561,563 B2
(45) Date of Patent: Feb. 18, 2020

(54) OPTIMAL DESIGN OF A LOWER LIMB EXOSKELETON OR ORTHOSIS

(71) Applicant: Massachusetts Institute of Technology, Cambridge, MA (US)

(72) Inventors: Hugh M. Herr, Somerville, MA (US); Luke M. Mooney, Westford, MA (US); Elliott J. Rouse, Chicago, IL (US); Jiun-Yih Kuan, Cambridge, MA (US); Kenneth A. Pasch, Dover, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1349 days.

(21) Appl. No.: 14/572,499

(22) Filed: Dec. 16, 2014

(65) Prior Publication Data
US 2015/0209214 A1 Jul. 30, 2015

Related U.S. Application Data

(60) Provisional application No. 61/916,692, filed on Dec. 16, 2013, provisional application No. 62/014,377, filed on Jun. 19, 2014.

(51) Int. Cl.
*A61H 3/00* (2006.01)
*B25J 9/00* (2006.01)
(Continued)

(52) U.S. Cl.
CPC .............. *A61H 3/00* (2013.01); *A61F 2/605* (2013.01); *A61F 2/64* (2013.01); *A61F 2/6607* (2013.01);
(Continued)

(58) Field of Classification Search
CPC .............. A61H 3/00; A61F 2/605; A61F 2/64
See application file for complete search history.

(56) References Cited

U.S. PATENT DOCUMENTS

| 420,179 A | 1/1890 | Yagn |
|---|---|---|
| 438,830 A | 10/1890 | Yagn |

(Continued)

FOREIGN PATENT DOCUMENTS

| CN | 101584618 A | 11/2009 |
|---|---|---|
| CN | 102614066 A | 8/2012 |

(Continued)

OTHER PUBLICATIONS

Bogue, R. "Exoskeletons and Robotic Prosthetics: A Review of Recent Developments," *Industrial Robot: An International Journal*, 36(5): 421-427 (2009).

(Continued)

*Primary Examiner* — LaToya M Louis
(74) *Attorney, Agent, or Firm* — Hamilton, Brook, Smith & Reynolds, P.C.

(57) ABSTRACT

A link extends between a distal member and a proximal member of a wearable device, such as an exoskeleton, orthosis or prosthesis for a human lower limb. One or other of the distal member and the proximal member includes a crossing member. The link extends from the crossing member of the distal member or the proximal member, to the other of the distal member or the proximal member. Actuation of the link translates to a force at the distal or proximal member that is normal to a major longitudinal axis extending through the distal and proximal members. In one embodiment, a sliding link of a device configured for use with a human joint tracks two degrees of freedom of the joint.

61 Claims, 29 Drawing Sheets

(51) Int. Cl.
  *A61F 2/60* (2006.01)
  *A61F 2/64* (2006.01)
  *A61F 2/66* (2006.01)
  *A61H 1/02* (2006.01)

(52) U.S. Cl.
  CPC .......... *A61H 1/024* (2013.01); *A61H 1/0244* (2013.01); *A61H 1/0266* (2013.01); *B25J 9/0006* (2013.01); *A61H 2201/1215* (2013.01); *A61H 2201/1238* (2013.01); *A61H 2201/149* (2013.01); *A61H 2201/1409* (2013.01); *A61H 2201/1436* (2013.01); *A61H 2201/164* (2013.01); *A61H 2201/165* (2013.01); *A61H 2201/1628* (2013.01); *A61H 2201/1676* (2013.01); *A61H 2201/5007* (2013.01); *A61H 2201/5061* (2013.01); *A61H 2201/5069* (2013.01); *A61H 2201/5071* (2013.01); *A61H 2201/5082* (2013.01); *A61H 2201/5084* (2013.01); *A61H 2230/605* (2013.01)

(56) References Cited

U.S. PATENT DOCUMENTS

| | | | |
|---|---|---|---|
| 440,684 | A | 11/1890 | Yagn |
| 3,449,769 | A | 6/1969 | Mizen |
| 4,986,280 | A | 1/1991 | Marcus et al. |
| 5,016,869 | A | 5/1991 | Dick et al. |
| 5,207,114 | A | 5/1993 | Salisbury, Jr. et al. |
| 6,606,921 | B2 | 8/2003 | Noetzold |
| 6,719,671 | B1 | 4/2004 | Böck |
| 6,741,911 | B2 | 5/2004 | Simmons |
| 7,313,463 | B2 | 12/2007 | Herr et al. |
| 7,736,254 | B2 | 6/2010 | Schena |
| 8,244,402 | B2 | 8/2012 | Wells et al. |
| 8,483,816 | B1 | 7/2013 | Payton et al. |
| 8,500,823 | B2 | 8/2013 | Herr et al. |
| 8,512,415 | B2 | 8/2013 | Herr et al. |
| 8,801,641 | B2 | 8/2014 | Kazerooni et al. |
| 8,945,028 | B2 | 2/2015 | Kazerooni et al. |
| 9,060,884 | B2 | 6/2015 | Langlois |
| 9,289,316 | B2 | 3/2016 | Ward et al. |
| 9,498,401 | B2 | 11/2016 | Herr et al. |
| 9,682,005 | B2 | 6/2017 | Herr et al. |
| 9,889,058 | B2 * | 2/2018 | Horst .............. A61H 1/024 |
| 2004/0127825 | A1 | 7/2004 | Castillo |
| 2006/0004307 | A1 | 1/2006 | Horst |
| 2006/0150753 | A1 | 7/2006 | Massimo et al. |
| 2006/0211956 | A1 | 9/2006 | Sankai |
| 2007/0149328 | A1 | 6/2007 | Townsend |
| 2008/0009771 | A1 | 1/2008 | Perry et al. |
| 2009/0055019 | A1 | 2/2009 | Stiehl et al. |
| 2010/0241242 | A1 | 9/2010 | Herr et al. |
| 2010/0324699 | A1 | 12/2010 | Herr et al. |
| 2011/0040216 | A1 | 2/2011 | Herr et al. |
| 2011/0264230 | A1 | 10/2011 | Herr et al. |
| 2012/0179075 | A1 | 7/2012 | Perry et al. |
| 2012/0283845 | A1 | 11/2012 | Herr et al. |
| 2013/0150761 | A1 | 6/2013 | Romo |
| 2013/0158444 | A1 | 6/2013 | Herr et al. |
| 2013/0197318 | A1 | 8/2013 | Herr et al. |
| 2013/0282141 | A1 | 10/2013 | Herr et al. |
| 2013/0289452 | A1 | 10/2013 | Smith et al. |
| 2013/0296746 | A1 | 11/2013 | Herr et al. |
| 2013/0310979 | A1 | 11/2013 | Herr et al. |
| 2014/0257519 | A1 | 9/2014 | Herr et al. |
| 2014/0277739 | A1 * | 9/2014 | Kornbluh .............. B25J 9/0006 700/260 |
| 2015/0127118 | A1 | 5/2015 | Herr et al. |
| 2015/0173929 | A1 | 6/2015 | Kazerooni et al. |
| 2017/0246492 | A1 | 8/2017 | Herr et al. |
| 2017/0348176 | A1 | 12/2017 | Herr et al. |

FOREIGN PATENT DOCUMENTS

| | | |
|---|---|---|
| DE | 102 19 662 A1 | 11/2003 |
| GB | 2 260 083 A | 4/1993 |
| WO | WO 2009/149206 A2 | 12/2009 |
| WO | WO 2010/088635 | 8/2010 |
| WO | WO 2012/175211 A1 | 12/2012 |
| WO | WO 2013/142343 | 9/2013 |
| WO | WO 2014/151065 A2 | 9/2014 |
| WO | WO 2015/095211 A2 | 6/2015 |

OTHER PUBLICATIONS

Cherry, M.S. et al., "An Elastic Exoskeleton for Assisting Human Running," in *Proceedings of the ASME 2009 International Design Engineering Technical Conferences & Computers and Information in ENgineering Conference*, pp. 1-12 (2009).

Cyberdyne, "What's 'HAL' (Hybrid Assistive Limb®)?" Available at: http://www.cyberdyne.jp/english/robotsuithal/ (Retrieved from Internet on Jan. 14, 2014).

Grabowski, A.M., and Herr, H.M., "Leg Exoskeleton Reduces the Metabolic Cost of Human Hopping," *Journal of Applied Physiology*, 107: 670-678 (2009).

Karlin, S., "Raiding Iron Man's Closet," *IEEE Spectrum*, 48(8), p. 25 (Aug. 2011).

Kazerooni, H, et al., "On the Control of the Berkeley Lower Extremity Exoskeleton (BLEEX)," in *Proceedings of IEEE International Conference on Robotics and Automation*, pp. 4353-4360 (Aug. 2005).

Kuan, J. (Jarvis), et al., "Tethered Wearable Robot System for Augmentation and Rehabilitation," *Biomechatronics Group, Media Lab, Massachusetts Institute of Technology*, (Nov. 6, 2012).

Kuan, J. et al., "Design of a Knee Joint Mechanism that Adapts to Individual Physiology," *Engineering in Medicine and Biology Society (EMBS)*, 2014, 36$^{th}$ Annual Conference of the IEEE, pp. 2061-2064 (Aug. 26-30, 2014).

Lockheed Martin, Product Finder, Press Releases, "HULC", Available at: http://www.lockheedmartin.com/products/hulc/ (Retrieved from the Internet on Jan. 15, 2014).

Mooney, L.M., et al., "Autonomous exoskeleton reduces metabolic cost of human walking during load carriage", *Journal of NeuroEngineering and Rehabilitation*, 11:80 (2014).

PRNewswire, Raytheon Unveils Lighter, Faster, Stronger Second Generation Exoskeleton Robotic Suit (Sep. 27, 2010; Available at: http://multivu.prnewswire.com/mnr/raytheon/46273 (Retrieved from the Internet on Jan. 21, 2014).

Walsh, C.J., et al., "A Quasi-Passive Leg Exoskeleton for Load-Carrying Augmentation," *International Journal of Humanoid Robotics*, 4: 487-506 (2007).

Zelinsky, A., "Robot Suit Hybrid Assistive Limb," *IEEE Robotics & Automation Magazine*, 16(4): pp. 98 and 102 (2009).

Hugh Herr: "The new bionics that let us run, climb and dance", TED 2014; Filmed Mar. 2014; Available at: https://www.ted.com/talks/hugh_herr_the_new_bionics_that_let_us_run_climb_and_dance (Retrieved from the Internet on Apr. 15, 2015).

Alexander, R. M., "Energy-saving mechanisms in walking and running," *Journal of Experimental Biology*, 160:55-69 (1991).

Au, S. K., et al., "Biomechanical Design of a Powered Ankle-Foot Prosthesis," Proceedings IEEE 10$^{th}$ International Conference on Rehabilitation Robotics, Noordwijk, The Netherlands (Jun. 2007).

Au, S. K., et al., "Powered Ankle-Foot Prosthesis for the Improvement of Amputee Ambulation," 29$^{th}$ IEEE Conference, Lyon, France (Aug. 2007).

Au, S., "Powered ankle-foot prosthesis for the improvement of amputee walking economy," Doctoral dissertation, Massachusetts Institute of Technology (2007).

Belli, A., et al., "Moment and power of lower limb joints in running," *International Journal of Sports Medicine*, 23:136-141 (2002).

Biewener, A. A., "Muscle function in vivo: A comparison of muscles used for elastic energy savings versus muscles used to generate mechanical power," *American Zoology*, 38:703-717 (1998).

(56) References Cited

OTHER PUBLICATIONS

Blaya, J. A. and Herr, H., "Adaptive control of a variable-impedance ankle-foot orthosis to assist drop-foot gait," IEEE Transactions on Neural Systems & Rehabilitation Engineering.12(1):24-31 (2004).

Brockway, J. M., et al., "Derivation of formulae used to calculate energy expenditure in man," *Human Nutrition Clinical Nutrition*, 41:463-471 (1987).

Cavagna, G. A., "Force platforms as ergometers," *Journal of Applied Physiology*, 39(1):174-179 (1985).

Cavagna, G. A., et al., "Mechanical work in terrestrial locomotion: Two basic mechanisms for minimizing energy expenditure," *American Journal of Physiology Regulatory, Integrative, and Comparitive Physiology*, 233:243-261 (1977).

Clancy, E. A., et al., "Sampling, noise-reduction, and amplitude estimation issues in surface electromyography," *Journal of Electromyography and Kinesiology*, 12:1-6 (2002).

Collins, J. A., "*Mechanical Design of Machine Elements and Machines*," John Wiley and Sons, Hoboken, N.J., Table of Contents (2003).

Collins, S. H., "Exploring ankle control strategies with an experimental biomechatronic testbed", *Dynamic Walking*, 2011 International Conference on.—Abstract (Jul. 2011).

Collins, S. H., "Exploring ankle control strategies with an experimental biomechatronic testbed", *Dynamic Walking*, 2011 International Conference on.—Slides (Jul. 2011).

Cram, J. R., et al., "*Introduction to Surface Electromyography*," Aspen Publishers, Inc., Table of Contents (1998).

Dollar, A. M. and Herr, H., "Active orthoses for the lower-limbs—Challenges and state of the art," *Proceedings of the 2007 IEEE International Conference on Rehabilitation Robotics (ICORR)*, Noordwijk, Netherlands, pp. 968-977, Jun. 2007.

Dollar, A. M. and Herr, H., "Design of a quasi-passive knee exoskeleton to assist running," Proceedings of the 2008 IEEE/RSJ International Conference on Intelligent Robots and Systems, Nice, France, Sep. 2008.

Dollar, A. M. and Herr, H., "Lower extremity exoskeletons and active Orthoses," Challenges and state-of-the-art, *IEEE Transactions on Robotics*, 24(1):144-158 (2008).

Elliott, G. A., "Design and Evaluation of a Quasi-Passive Robotic Knee Brace: On the Effects of Parallel Elasticity on Human Running." Doctoral dissertation, Massachusetts Institute of Technology (2012).

Elliott, G. et al., "The Biomechanics and Energetics of Human Running using an Elastic Knee Exoskeleton," *International Conference on Rehabiliation Robotics* (2013).

Farley, C. T. and Ferris, D.P., "Biomechanics of walking and running: From center of mass movement to muscle action," *Exercise and Sport Sciences Reviews*, 26(1):253-285 (1998).

Farley, C. T. and Gonzalez, O., "Leg stiffness and stride frequency in human running," *Journal of Biomechanics*, 29(2):181-186 (1996).

Farris, D. J. and Sawicky, G. S., "The mechanics and energetics of human walking and running: A joint level perspective," Journal of the Royal Society Interface, 9(66): 110-118 (2012).

Ferris, D. P., "Running in the real world: Adjusting leg stiffness for different surfaces," *Proceedings Biological Sciences*, 265: 989-994 (1998).

Ferris, D. P., et al., "Neuromechanical adaptation to hopping with an elastic ankle-foot orthosis," *Journal of Applied Physiology*, 100: 163-170 (2006).

Ferris, D. P., et al., "Runners adjust leg stiffness for their first step on a new running surface," *Journal of Biomechanics*, 32:787-794 (1999).

He, J., et al., "Mechanics of running under simulated low gravity," *Journal of Applied Physiology*, 71:863-870 (1991).

Herr, H. and Langman, N., "Optimization of human-powered elastic mechanisms for endurance amplification," *Structural Optimization*, 13(1): 65-67 (Feb. 1997).

Herr, H. M. et al. "Patient-adaptive prosthetic and orthotic leg systems," Proceedings of the 12th Nordic Baltic Conference on Biomedical Engineering and Medical Physics, Reykjavik, Iceland, pp. 123-128 (Jun. 2002).

Herr, H., "Exoskeletons and orthoses: classification, design challenges and future directions," *Journal of NeuroEngineering and Rehabilitation*, 6(1): (2009).

HULC-Lockheed Martin, www.lockheedmartin.com/us/products/hulc.html (Downloaded Jan. 15, 2014).

Kawamoto, H. and Sankai, Y., "Power assist method based on phase sequence and muscle force condition for HAL," *Advanced Robotics*, 19 (7):717-734 (2005).

Kazerooni, H. and Kim, S., "Contact instability of the direct drive robot when constrained by a rigid environment," In *ASME Winter Annual Meeting*, (1989).

Kerdok, A. E., et al., "Energetics and mechanics of human running on surfaces of different stiffnesses," *Journal of Applied Physiology*, 92:469-478 (2002).

Lee, C. R. and Farley, C.T., "Determinants of the center of mass trajectory in human walking and running," *Journal of Experimental Biology*, 201: 2935-2944 (1998).

Martinez-Villalpando, E. C., "Design and Evaluation of a Biomimetic Agonist-Antagonist Active Knee Prosthesis." Doctoral dissertation, Massachusetts Institute of Technology (2012).

Martínez-Villalpando, E. C., et al., "Design of an agonist-antagonist active knee prosthesis," IEEE conference, *Biomedical Robotics and Biomechatronics*, Scottsdale, AZ (Oct. 2008).

McMahon, T. A. and Cheng, G. C., "The mechanics of running: How does stiffness couple with speed?" *Journal of Biomechanics*, 23(1):65-78 (1990).

McMahon, T. A., "*Muscles, Reflexes, and Locomotion*," Princeton University Press, Princeton, N.J., Table of Contents (1984).

Merletti, R., Standards for reporting EMG data, Technical report, Politecnico di Torino (1999).

Mosher, R. S., "Handyman to Hardiman," Technical report, General Electric Research and Development Center (1967).

Munro, C. F., et al., "Ground reaction forces in running: a reexamination," *Journal of Biomechanics*, 20(2):147-155 (1987).

Novacheck, T. F., "The biomechanics of running", *Gait and Posture*, 7: 77-95 (1998).

Pratt, G. A. and Williamson, M. M., "Series elastic actuators," In *IEEE International Conference on Intelligent Robots and Systems*, 1:399-406 (1995).

Sawicki, G. S. and Ferris, D. P., "Mechanics and energetics of incline walking with robotic ankle exoskeletons," *The Journal of Experimental Biology*, 212:32-41 (2008).

Stock Drive Products, *Elements of Metric Gear Technology*, New Hyde Park, NY, at least as early as Jan. 15, 2014.

Valiente, A., "Design of a quasi-passive parallel leg exoskeleton to augment load carrying for walking," Master's thesis, Massachusetts Institute of Technology (2005).

Walsh C. J., et al., "Development of a lightweight, underactuated exoskeleton for load-carrying augmentation," *Proceedings of the IEEE International Conference on Robotics and Automation*, Orlando, FL, (May 2006).

Walsh, C. J. et al., "An autonomous, underactuated exoskeleton for load-carrying augmentation," *IEEE/RSJ International Conference on Intelligent Robots and Systems (IROS)*, Beijing, China, Oct. 2006.

Walsh, C. J., "Biomimetic design of an under-actuated leg exoskeleton for load-carrying augmentation," Master's thesis, Massachusetts Institute of Technology (2006).

Wiggin, M. B., et al., "An exoskeleton using controlled energy storage and release to aid ankle propulsion," In *2011 IEEE International Conference on Rehabilitation Robotics Rehab Week*, Zurich, Switzerland (Jun. 29-Jul. 1, 2011).

Zoss, A., et al., On the mechanical design of the Berkeley lower extremity exoskeleton (BLEEX), In *IEEE International Conference on Intelligent Robots and Systems* (2005).

Non-Final Office Action for U.S. Appl. No. 13/774,774, dated Mar. 7, 2016.

Asbeck, A.T., et al., "Biologically-inspired Soft Exosuit", *2013 IEEE Int'l Conf. on Rehabilitation Robotics*, Jun. 24-26, 2013.

(56) References Cited

OTHER PUBLICATIONS

International Search Report and Written Opinion of the International Searching Authority, PCT/US2014/070636, "Optimal Design of a Lower Limb Exoskeleton or Orthosis", dated Aug. 25, 2015.
Wehner, M., et al., "A Lightweight Soft Exosuit for Gait Assistance", *2013 IEEE Int'l Conf. on Robotics and Automation (ICRA)*, May 6-10, 2013.
Endo, K., "Human Walking Model Predicts Joint Mechanics, Electromyography and Mechanical Economy," IEEE/RSJ International Conference on Intelligent Robots and Systems (Oct. 11-15, 2009).
Endo, K., "A Model of Muscle-Tendon Function in Human Walking," IEEE International Conference on Robotics and Automation (May 12-17, 2009).
Haeufle, D.F.B., et al., "A Clutched Parallel Elastic Actuator Concept: Towards Energy Efficient Powered Legs in Prosthetics and Robotics," IEEE RAS/EMBS International Conference on Biomedical Robotics and Biomechatronics, (Jun. 24-27, 2012).
Bowden cable,"" Wikipedia. [Online]. Availableat: https://en.wikipedia.org/wiki/Bowden_cable.(Downloaded Jun. 1, 2017).
Buerger, S. P., "Stable, high-force, low-impedance robotic actuators for human-interactive machines," Massachusetts Institute of Technology (2006).
Kim, C. Y., et al., "Dynamic modeling of coupled tendon-driven system for surgical robot instrument," Int. J. Precis. Eng. Manuf., vol. 15, No. 10, pp. 2077-2084 (2014).
Kuan, J., et al., "Design of a Knee Joint Mechanism that Adapts to Individual Physiology," 36th Annu. Int. Conf. IEEE Eng. Med. Biol. Soc., pp. 2061-2064 (2014).
Letier, P., et al, "Bowden Cable Actuator for TorqueFeedback in Haptic Applications," Eurohaptics, 2006.
"Townsend and, W. T., et al., ""TeleoperatorSlave-WAM Design Methodology,"" Ind. Robot An Int. J., vol. 26, No. 3, pp. 167-177 (1999)."
Veneman, J. F., "A Series Elastic- and Bowden Cable-Based Actuation System for Use as Torque Actuator in Exoskeleton-Type Robots," Int. J. Rob. Res., vol. 25, No. 3, pp. 261-281 (2006).
International Preliminary Report on Patentability & Written Opinion of the International Searching Authority, PCT/US2014/070636, "Optimal Design of a Lower Limb Exoskeleton or Orthosis", dated Jun. 21, 2016.
Abul-Haj, C., & Hogan, N. "An emulator system for developing improved elbow-prosthesis designs," IEEE Transactions on Biomedical Engineering, 9:724-737 (1987).
Andersen, J. B., & Sinkjaer, T. "Mobile ankle and knee perturbator," IEEE Transactions on Biomedical Engineering, 50(10): 1208-1211 (2003).
Andersen, J. B.,& Sinkjaer, T. "An actuator system for investigating electrophysiological and biomechanical features around the human ankle joint during gait", IEEE Transactions on Rehabilitation Engineering, 3(4): 299-306 (1995).
Caputo, J. M. and Collins, S. H. (Aug. 2012) "Externally powered and controlled ankle-foot prosthesis," Annual meeting of American Society of Biomechanics, 2012—Poster.
Caputo, J. M. and Collins, S. H. (Aug. 2012) "Externally powered and controlled ankle-foot prosthesis," Annual meeting of American Society of Biomechanics, 2012.—Abstract.
Caputo, J. M., and Collins, S. H. (Jul. 2011) "Externally powered and controlled ankle-foot prosthesis," In Dynamic Walking, 2011 International Conference—Abstract.
Caputo, J. M., and Collins, S. H. (Jul. 2011) "Ankle-foot prosthesis testbed." In Dynamic Walking, 2011 International Conference—Poster.
Collins, S. H. (Jul. 2011) "Developing ankle control strategies with an experimental biomechatronic testbed," In Dynamic Walking, 2011 International Conference on.—Slides.
Collins, S. H. (Jul. 2011) "Exploring ankle control strategies with an experimental biomechatronic testbed," In Dynamic Walking, 2011 International Conference on.—Abstract.
Flowers, W. C. (1973). "A man-interactive simulator system for above-knee prosthetics studies," Dissertation, Massachusetts Institute of Technology.
Jackson, R. W. and Collins S. H. (May 2012) "Targeting specific muscles for rehabilitation with an EMG-controlled ankle-foot orthosis," In Dynamic Walking, 2012 International Conference—Slides.
Jackson, R. W. and Collins S. H. (May 2012) "Targeting specific muscles for rehabilitation with an EMG-controlled ankle-foot orthosis," In Dynamic Walking, 2012 International Conference—Abstract.
Sawicki, G. S., Gordon, K. E., & Ferris, D. P. (Jul. 2005). "Powered lower limb orthoses: applications in motor adaptation and rehabilitation," IEEE in Rehabilitation Robotics, 2005, ICORR 2005, 9$^{th}$ International Conference (pp. 206-211).
Schiele, A. "Fundamentals of Ergonomic Exoskeleton Robots." Doctoral dissertation, Ph.D. Thesis, Delft University of Technology, 2008, available at: www.library.tudelft.nl.
Sulzer, J. S., Holz, R. A., Peshkin,M, A., & Patton, J. L. "A highly backdrivable, lightweight knee actuator for investigating gait in stroke," IEEE Transactions on Robotics,, 25(3): 539-548 (2009).
Veneman, J. F. (2007). "Design and evaluation of the gait rehabilitation robot LOPES." University of Twente. Ph.D. Dissertation.
Office Action in regards to U.S. Appl. No. 13/722,246, entitled "A Robotic System For Simulating A Wearable Device And Method Of Use," dated Dec. 4, 2015.

\* cited by examiner

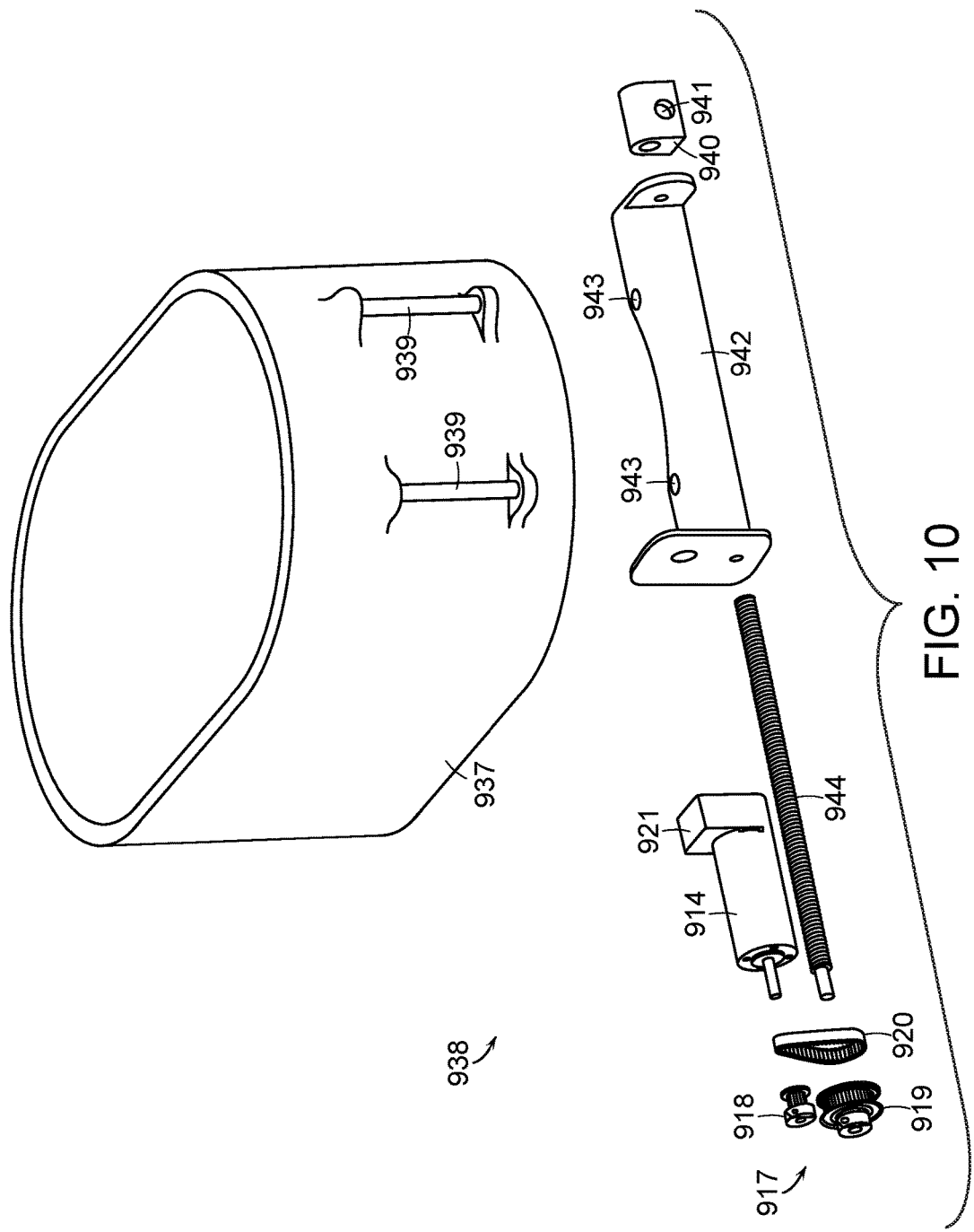

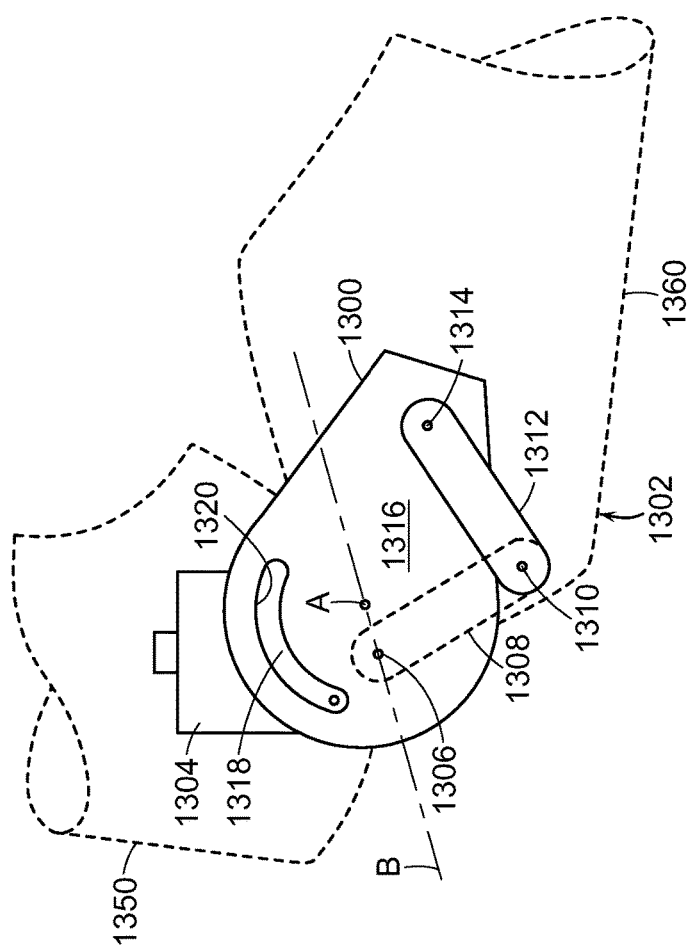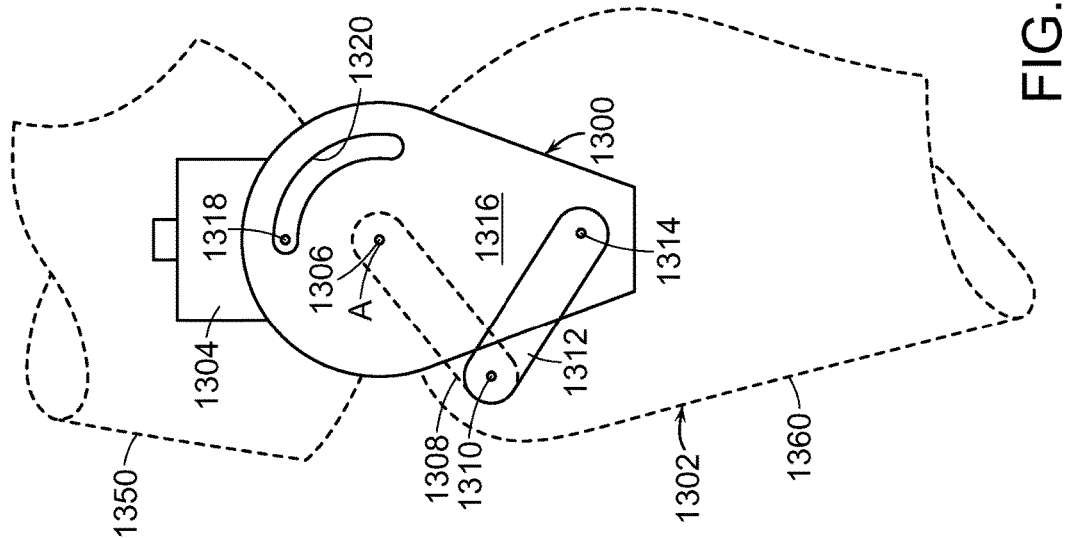

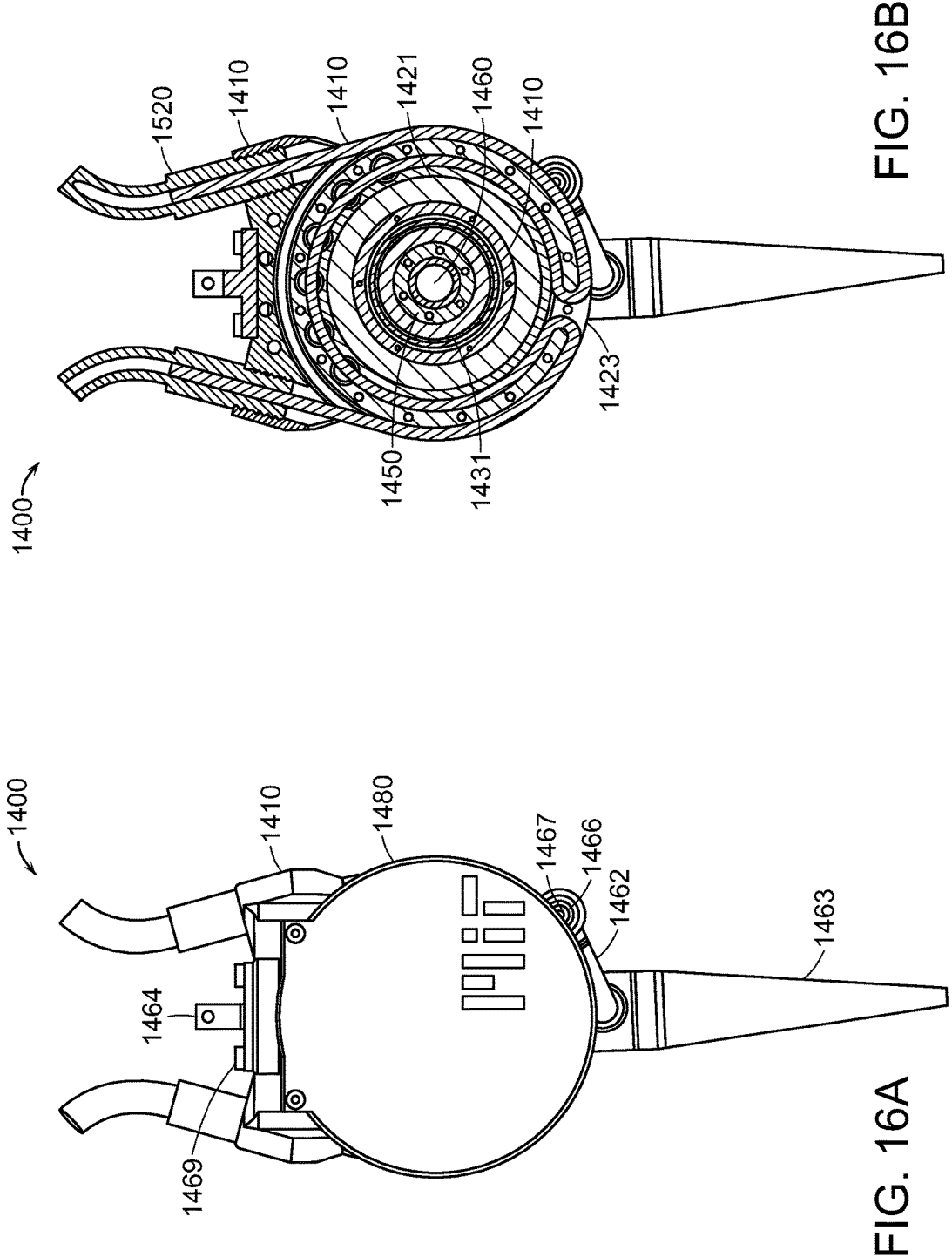

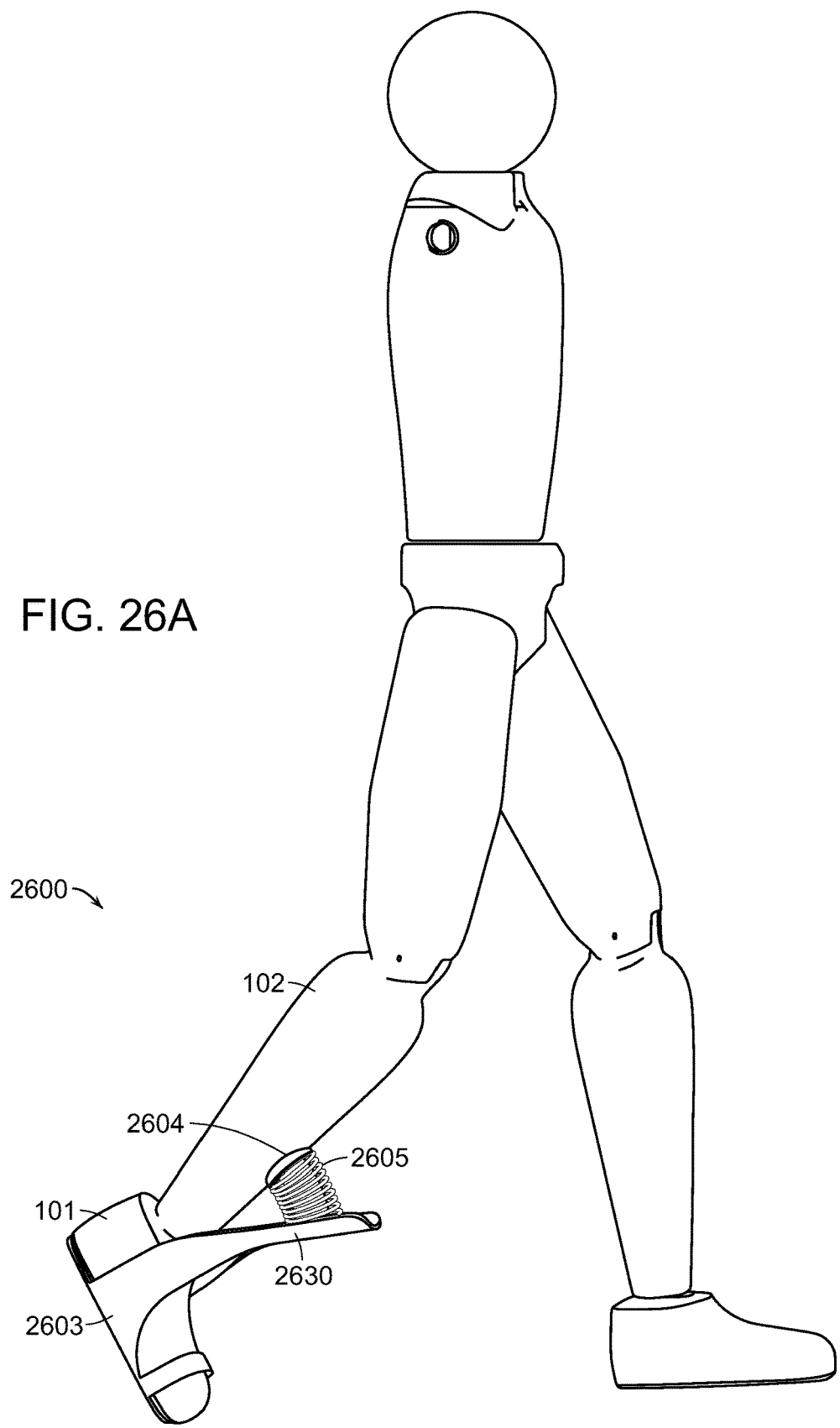

OPTIMAL DESIGN OF A LOWER LIMB EXOSKELETON OR ORTHOSIS

RELATED APPLICATIONS

This application claims the benefit of U.S. Provisional Application No. 61/916,692, filed on Dec. 16, 2013 and U.S. Provisional Application No. 62/014,377, filed on Jun. 19, 2014. The entire teachings of the above applications are incorporated herein by reference.

GOVERNMENT SUPPORT

This invention was made with Government support under Grant No. NNX12AM16G awarded by the National Aeronautics and Space Agency. The Government has certain rights in the invention.

BACKGROUND OF THE INVENTION

Exoskeletons, orthoses and prostheses are intended to enhance human function, often in the context of locomotory motion. Exoskeletons, for example, are worn on the body exterior, around a biological joint that is the target of an intended function (e.g., knee or hip). Depending on the exact purpose of the device, the mechanical effect of the exoskeleton may be to add, remove or store and release energy. Irrespective of purpose, however, all exchange of energy between a human user and a worn exoskeleton occurs through mechanical interaction between the exoskeleton and the human body. The mechanical interaction imparts force distributions on the soft tissue surrounding the joint and limb segments. Typically, the exoskeleton uses a mechanical joint in parallel with the anatomical joint, which reduces flexibility, or the force distributions are parallel to the axis of the limb (i.e. shear), which may be uncomfortable to the user. This discomfort often disrupts device function and hinders the efficacy of the exoskeleton.

International Application number WO2012/175211 A1, the teachings of which are incorporated herein in their entirety, describes a fully integrated system with artificial joints. Artificial joints generally reduce forces exerted on the human body, but often also greatly constrain motion and flexibility. Known powered exoskeletons are also typically heavy and cumbersome to use.

Conventional exoskeleton and assistive devices usually consist of active actuators, passive mechanical components, and mechanical interfaces. In order to reduce design complexity, limb joints are usually considered as one-to-three degrees of freedom (DOF) joints of multiple single DOF hinge joints in a single plane. However, biological joints are complex and usually rotate with respect to a changing instantaneous center. For example, knee motion may be visualized as rotation of a femur about a series of three-dimensional instantaneous axes rather than a single fixed axis. As a result, a mismatch between limb joint motion and mechanical interface motion typically leads to undesired ligament and muscle length changes and other internal mechanical changes. Those undesired effects contribute to discomfort, as well as to slippage and sluggish interaction with such devices.

Therefore, a need exists for devices, such as exoskeletons, orthoses and prostheses that overcome or minimize the above-referenced problems.

SUMMARY OF THE INVENTION

The invention is generally directed to a wearable device, such as a prosthesis, orthosis or exoskeleton, such as for use with the human biological ankle, knee or hip, or a lower limb of any combination of the human ankle, knee and hip. In one embodiment, the device includes a distal member wearable by an individual distal to a skeletal joint of the individual, a proximal member wearable by the individual proximal to the joint and a link between the distal and proximal member. One or the other of the distal member and the proximal member includes a crossing member, wherein the link extends from the crossing member of the distal member or the proximal member to the other of the distal member or the proximal member. Actuation of the link translates to a force at the distal or proximal member that is normal to a major longitudinal axis extending through the distal and proximal members when worn by the human individual.

In one embodiment, the crossing member is rigid. The crossing member can be rigidly or not rigidly fixed to one or the other of the distal member and the proximal member.

In a specific embodiment, the link includes a ball screw actuator. In another embodiment, the link and the crossing member are components of a series elastic actuator. The series elastic actuator can be, for example, a bidirectional actuator, such as a pneumatic actuator. An example of a suitable pneumatic actuator for use with the present invention includes a hardening series elastic element. In another embodiment, the pneumatic actuator includes an inflatable bladder. In still another embodiment, the series elastic actuator is a unidirectional actuator, such as a pneumatic actuator or an electric spool actuator.

The crossing member can include the distal end and proximal end, wherein the distal end is fixed to the distal member at one end and is essentially normal to a major longitudinal axis of the distal member, and wherein the link extends between the proximal end of the crossing member and the proximal member. In a specific embodiment, the distal member includes a surface that is essentially parallel to a plane that is normal to the major longitudinal axis extending between the distal and proximal members. In one embodiment, the device of the invention further includes a second crossing member extending from the distal member, wherein the crossing members are essentially parallel to each other.

In one embodiment of the invention, the distal member is configured to support and to be secured to a human foot, wherein the crossing members are configured to extend essentially dorsally and parallel to a tibia extending from the human foot, and wherein the proximal member is secured to a calf of the human, wherein an electric spool actuator includes a cable that is linked to the proximal end of the crossing member and spans the calf normally to a major longitudinal axis of the human tibia, whereby actuation of the actuator causes rotation of the distal member about human ankle joint to thereby at least assist plantar flexion of the human foot while walking.

In another embodiment, the crossing member is not rigid. In this embodiment, the link includes a strut extending from the proximal member to the distal member, whereby the crossing member and the strut span the axis about which the distal member rotates. In a specific embodiment, the strut is constrained at the proximal member normally and laterally to a major longitudinal axis of the crossing member extending from the proximal number to the distal member, wherein the strut is not restricted along the major longitudinal axis of the crossing member. In this embodiment, the link further includes at least one roller at the proximal member that constrains the strut normally and laterally. The link includes at least one pair of rollers in opposition to each other, wherein the strut is normally constrained between the pair of rollers. The strut can be curved at the pair of rollers, whereby shear force between the strut and pair of rollers during rotation of the distal member of the axis spanned by the crossing member and the strut is less than it would be if the strut were straight at the pair of rollers. The strut includes a guide tube at the pair of rollers, wherein the crossing member extends through the guide tube. In one embodiment, the device includes a pair of crossing members and a pair of struts. In a specific embodiment, the struts are essentially straight between the rollers and the distal member. In one particular embodiment, at least one of the struts deflects during eversion and inversion of the human foot secured to the distal member and a human calf secured to the proximal member. Typically, the struts are rigid. In one embodiment, the struts are curved, whereby the struts operate as series springs during a normal walking cycle of human foot secured to the distal member and the human calf secured to the proximal member.

In one embodiment, the link further includes a winch actuator assembly attached to a proximal end of the pair of crossing members, whereby actuation of the link will cause retraction of the crossing members, which causes rotation of the distal member and plantar flexion of the human foot secured to the distal member about a human ankle joint. In another embodiment, the pair of crossing members is fixed to a proximal end of the distal member. A second pair of crossing members can be fixed to a distal end of the distant member. In one specific embodiment, the link further includes a second winch actuator assembly attached to a proximal end of the second pair of crossing members, whereby selective actuation of the link causes retraction of the second pair of crossing members, which causes rotation of the distal member and dorsiflexion of the human foot secured to the distal member about the human ankle joint. In a specific embodiment, the distal members are configured to fit the human calf. In this embodiment, the proximal member can be configured to fit the human thigh. In one embodiment, the crossing member extends proximally from the distal member, and the link extends between the proximal member and a proximal end of the crossing member, whereby actuation of the link will cause extension of a human leg secured to the proximal and distal members. Alternatively, the crossing member extends distally from the proximal member and the link extends between a distal end of the crossing member and the distal member, whereby actuation of a link will cause extension of the human leg secured to the proximal and distal members.

In another embodiment, the proximal member is configured to fit a human waist. In this embodiment, the distal member is configured to fit a human thigh. Preferably, the crossing member extends proximally from the distal member. In one such embodiment, the link includes a bidirectional actuator, whereby actuation of the link will rotate the distal member and a human thigh secured to the distal member about a hip joint of a human wearing the device. In one embodiment, the bidirectional actuator is a ball screw actuator.

Another embodiment of the device is a wearable lower limb device that includes a distal module wearable by an individual that spans a distal skeletal joint and a proximal module wearable by the individual that spans a proximal skeletal joint, wherein the distal module and the proximal module are coupled. At least one of the distal and proximal modules includes a distal member wearable by the individual distal to the respective skeletal joint, a proximal member wearable by the individual proximal to the respective skeletal joint, and a link between the distal and proximal members, whereby actuation of the link will be translated to a force at the distal or proximal member that is normal to a major longitudinal axis extending through the distal and proximal members. In this embodiment, optionally, at least one of the other of the distal member and proximal member includes a crossing member, and the link extends from the crossing member of the distal member or the proximal member to the other of the distal member or the proximal member. In one specific embodiment, both the distal module and the proximal module include a distal member, a proximal member, a crossing member and a link. The distal module and the proximal module can be coupled by a common member, wherein the proximal member of the distal module is also at least a component of the distal member of the proximal module. The distal module and the proximal module can be rigidly coupled. In one embodiment, the common member includes a degree of freedom coupling the distal module to the proximal module. For example, the degree of freedom can be a hinge causing rotation in a plane essentially parallel to a plane of rotation of at least one of the proximal module and distal module. The distal module can be, for example, an exoskeleton, orthosis or prosthesis configured for use with a human knee joint, while the proximal module can be an exoskeleton, orthosis or prosthesis configured for use with a human hip joint. In a specific embodiment, the link of the distal and proximal modules can each include a winch actuator or a ball screw actuator. In one particular preferred embodiment, the crossing member of the distal module includes a pulley and a cord linking the pulley, and a link of the distal module includes a winch actuator, whereby actuation of the link of the distal module causes extension of the human knee secured to the distal module. The distal member of the distal module can include, for example, a leaf spring linking the pulley to the distal member of the display module. In one embodiment, the crossing member of the distal module extends proximally from the hinge of the distal member of the proximal module. The link of the proximal module can include a cord and a winch actuator that is at the proximal member of the proximal module, wherein the cord extends from the crossing member of the proximal module to the winch actuator, whereby actuation of the link of the proximal module will cause flexion movement of a human hip secured to the proximal module. In an alternate embodiment, the link of the proximal module includes a ball screw actuator, whereby actuation of the link is bidirectional and, selectively causes flexion and extension of a human hip secured to the proximal member.

In another embodiment, the lower limb device further includes an ankle module that is distal to the distal module, wherein the ankle module is coupled to the distal module, and wherein the distal module and the ankle module share a common member. In one embodiment of this example, the ankle module includes an ankle distal member, an ankle proximal member, and an ankle link between the ankle distal number and the ankle proximal member, whereby actuation of the ankle link will be translated to a force at the ankle distal member or the ankle proximal member that is normal to a major longitudinal axis extending through the ankle distal end ankle proximal members. In one such embodiment of the lower limb device, at least one or the other of the ankle distal and the ankle proximal member includes an ankle crossing member, wherein the ankle link extends from the ankle crossing member of the ankle distal member or the ankle proximal member to the other of the ankle distal member or the ankle proximal member.

In one embodiment the crossing member of the ankle module extends proximally from the distal member of the ankle module. In a particular embodiment, the link of the ankle module includes a winch actuator at the proximal member of the ankle module, wherein a cord of the winch actuator extends from a proximal end of the crossing member to the winch actuator of the ankle module, whereby actuation of the link causes plantar flexion of a human ankle secured to the ankle module.

The wearable lower limb device of the invention can be, for example, an exoskeleton, orthosis or prosthesis for a human ankle, and the proximal module can be an exoskeleton, orthosis or prosthesis for a human knee.

In one embodiment, the wearable device includes a link that applies a substantially linear force to the crossing member.

In still another embodiment, the device of the invention includes a ground link that is fixed relative to either a distal end of a human femur or a proximal end of a human tibia. An input link having a first end and a second end is fixed to and rotates about a pivot defining an axis of rotation, wherein the pivot links the input link at the first end to the ground link. A coupler having a first end and a second end is pivotally mounted to the second end of the input link. An output link is fixed relative to the other of the distal end of the human femur or the proximal end of the human tibia and has a first end and a second end, the first end being pivotally mounted at the first end to the second end of the coupler. A sliding link is located between the ground link and the output link, whereby rotation of the human knee joint to which the device is secured will cause translation of an axis of rotation of the output link relative to the ground link to track two degrees of freedom of the human knee joint, wherein the human knee joint rotates in a sagittal plane about an axis that is normal to the sagittal plane but which moves relative to the axis of rotation of the pivot linking the first end of the input link to the ground link. In this embodiment, the sliding link includes a slot defined by the output link, wherein a protrusion from the ground link extends through the slot defined by the sliding link, the sliding link restricting movement of the axis of rotation of the output link to a line normal to an axis of rotation of the pivot.

One purpose of this invention is to modify the force distributions of an exoskeleton, orthosis or prosthesis on a limb. The intent is to alter the forces such that they are no longer parallel to the axis of the limb, but instead, perpendicular to the axis, whereby loading will be substantially more comfortable.

Another purpose of this invention is to transmit planetary torques from either active or passive devices to limbs without altering the normal biological joint motions. The intent is to apply torques to a limb by utilizing an unconstrained multiple DOF mechanism, thereby providing an adaptive trajectory of instantaneous centers of the device matching that of the biological joints.

The device of the present invention employs a geometric configuration that does not require artificial joints, therefore, making the device more comfortable and lighter. The comfort and weight of the device of the invention plays a large role in its ability to augment or rehabilitate the physical capabilities of an individual wearing the device.

The device of the invention can constrain the linkage system and set trajectories of instantaneous centers of the device in accordance with normal biological joint motions while the external sources apply torques to the joint at the same time. As a result, mismatch between limb joint motion and mechanical interface motion is largely avoided, as well as skin shear force, undesired slippage and sluggish interaction between the individual and the device.

The device of the invention can also act in the sagittal plane so that external sources can apply torques to joints of the individual without impeding rotation of the joint in the other planes, i.e., coronal or transverse. As a result, mismatch between biological ankle joint motion and mechanical interface motion is greatly avoided, as well as undesired large additional inertia added by the device worn by the individual.

In still another aspect of this invention, a force balance transmission is maintained in the sagittal plane of the individual so that external sources can apply torques to the biological joint in the sagittal plane without impeding rotation of the biological joint in the other two planes. The device of the invention also avoids significant skin shear force at the mechanical interface with the individual wearer. As a result, mismatch between ankle joint motion, for example, and mechanical interface motion is substantially avoided, as well as undesired large additional inertia added by the device of the invention.

Potential commercial applications of the present invention include enhanced human locomotory function. Specifically, enhancement may center on modification of ambulation of able-bodied persons or individuals with movement pathology. For use in able-bodied individuals, the invention can enhance locomotory function beyond what is otherwise physiologically possible. For example, physical enhancement could be employed to assist professional duties (such as military or civil service duties), athletic achievement, recreation, or other opportunities. Furthermore, gait dysfunction resulting from movement pathology, such as Parkinson's disease or knee osteoarthritis, or restoration of age-related reduced locomotory function could be treated or relieved by this invention. Each of these potential applications highlights the commercial possibilities associated with an exoskeleton with improved loading distribution.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 10 is an exploded view of a hip exoskeleton ball screw actuator component of the embodiment of the invention shown in FIG. 9.

FIGS. 13A-B illustrate a two-DOF five-bar linkage system applied to a knee joint.

FIG. 16A is a frontal view of the joint mechanism of FIG. 14.

FIG. 16B is a cross sectional front view of the joint mechanism of FIG. 14.

FIG. 26A is a perspective view of another embodiment of a device of the invention as worn by an individual, and includes an ankle exoskeleton with an inflatable bladder actuator.

DETAILED DESCRIPTION OF THE INVENTION

Figure 1:
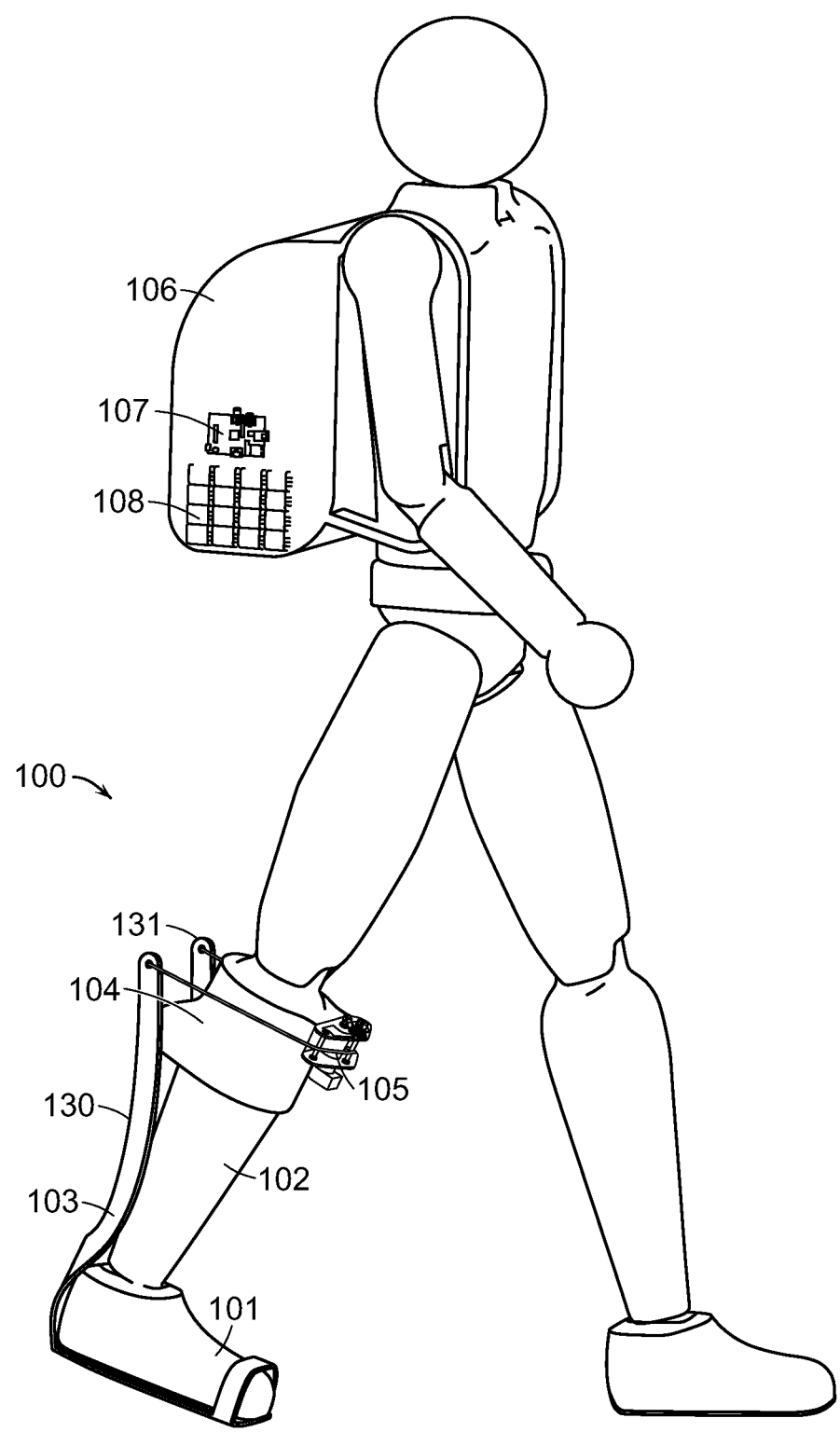
FIG. 1 is a perspective view of one embodiment of a device of the invention as worn by an individual, and includes an ankle exoskeleton with an electric spool actuator.

A description of example embodiments of the invention follows.

The invention is directed to an assistive or augmenting device that physically interacts with a person. One part of the invention is directed to a lower limb joint exoskeleton that physically interfaces with a person. A second part of the invention is directed to a joint exoskeleton or assistive device that physically interfaces with a person without having a significant mismatch between limb joint motion and mechanical interface motion in the same plane. A third part of the invention is directed to an ankle joint exoskeleton or assistive device that interfaces with a person without adding significant additional leg inertia to the human body or impeding ankle joint motion. A fourth part of the invention is directed to a device that enables external-internal rotation and inversion-eversion rotation while applying a torque in the sagittal plane, so that an attached biological ankle joint can maintain the normal gait. A fifth part of the invention is directed to a device that augments a hip, knee and ankle while minimizing shear on skin.

Part I:

In one embodiment, the invention is directed to a wearable device, such as a lower limb exoskeleton that mechanically interacts with human joints of a lower extremity while maintaining joint flexibility and reducing shear on skin. In one embodiment of the invention, to maintain joint flexibility and reduce weight and complexity, the device of the invention does not have a mechanical joint in parallel with the anatomical joint. Rather, it has at least one component distally attached to the human body with respect to the anatomical joint and at least one component proximally attached to the body with respect to the anatomical joint. An actuator exerts a force between these components in order to reduce reactive shear stress on the skin. In other words, the forces are generally applied in a normal direction (i.e. perpendicular) to the body's surface. The details of this embodiment of the invention are explained below.

2.1 Device Attachment

In one embodiment, one or the other of the distal member and the proximal member includes a crossing member, wherein the link extends from the crossing member of the distal member or the proximal member to the other of the distal member or the proximal member. In one specific embodiment, the crossing member is rigid. The crossing member can be rigidly fixed to one or the other of the distal member in the proximal member.

In a specific embodiment, the link includes a ball screw actuator. In another embodiment, the link and the crossing member are components of a series elastic actuator. The series elastic actuator can be, for example, a bidirectional actuator, such as a pneumatic actuator. An example of a suitable pneumatic actuator for use with the present invention includes a hardening series elastic element. In another embodiment, the pneumatic actuator includes an inflatable bladder. In still another embodiment, the series elastic actuator is a unidirectional actuator, such as a pneumatic actuator or an electric spool actuator.

The crossing member can include the distal end and proximal end, wherein the distal end is fixed to the distal member at one end and is essentially normal to a major longitudinal axis of the distal member, and wherein the link extends between the proximal end of the crossing member and the proximal member. In a specific embodiment, the distal member includes a surface that is essentially parallel to a plane that is normal to the major longitudinal axis extending between the distal and proximal members. In one embodiment, the device of the invention further includes a second crossing member extending from the distal member, wherein the crossing members are essentially parallel to each other.

In one embodiment of the invention, the distal member is configured to support and to be secured to a human foot, wherein the crossing members are configured to extend essentially dorsally and parallel to a tibia extending from the human foot, and wherein the proximal member is secured to a calf of the human, wherein an electric spool actuator includes a cable that is linked to the proximal end of the crossing member and spans the calf normally to a major longitudinal axis of the human tibia, whereby actuation of the actuator causes rotation of the distal member about human ankle joint to thereby at least assist plantar flexion of the human foot while walking.

In one embodiment, the link between the proximal and distal members applies only a substantially linear force to the crossing member(s).

In a specific embodiment, shown in FIGS. 1-3, 6-8 and 9 exoskeleton 100, 600, 900 includes at least one component attached to the body on the distal side of a joint, known as the "distal member" 103, 624, 934, respectively, and at least one component attached to the body on the proximal side of a joint, known as "proximal member" 104, 626, 937, respectively. A joint element includes a connection (e.g., pin or bearing, etc.) between the two members that constrains the motion in a manner similar to the anatomical joint. The distal member and proximal member are not connected with a joint element, and thus maintain the full range of motion of the anatomical joint.

Figures 2A, 2B:
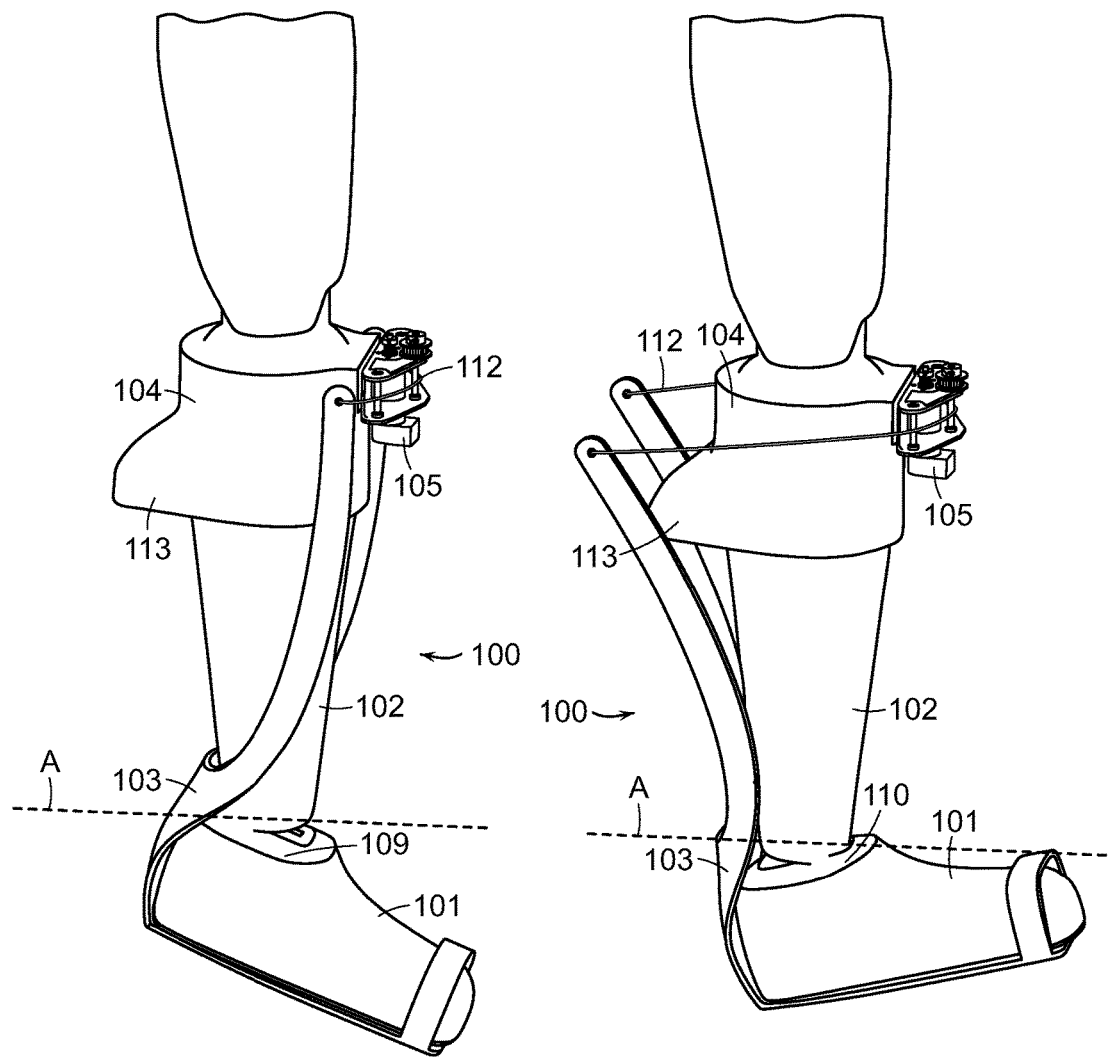
FIG. 2A is another perspective view of the embodiment of FIG. 1, wherein the device is in plantar flexion.
FIG. 2B is still another perspective view of the embodiment of FIG. 1, wherein the device is in dorsiflexion.

While the distal member and proximal member are attached to the body on their respective sides of the joint, one of the members extends through a virtual horizontal plane "A" that passes through the joint center of rotation 109, 110 of FIGS. 2A and 2B, respectively; this member is called the "crossing member." A member which spans a horizontal joint plane will be referred to as a "crossing member" and a member which does not cross the horizontal joint plane will be referred to as a "non-crossing member." For example, distal members 103 (FIGS. 1, 2A and 2B), 624 (FIGS. 6, 7A and 7B), and 934 (FIG. 9) in the depicted ankle, knee and hip exoskeletons, respectively, are rigidly fixed to crossing members 130, 632, and 936, respectively, and proximal members 104, 626, 937 are non-crossing members Ankle and knee exoskeletons of this invention also each have medial crossing members 131, 633 and lateral crossing members 130, 632. These distinctions are made because either the proximal or distal member can be rigidly fixed to the crossing member or include a crossing member. In one embodiment, the crossing member itself is rigid. In another embodiment, the crossing member is flexible, as shown, for example, in the device represented in FIGS. 19A and 19B. In still another embodiment, the crossing member, such as the crossing member in any of FIG. 1, 2A, 2B, 6, 7A, 7B or 9, is semi-rigid in that flexibility is tuned for delivering mechanical power amplification, to thereby operate in the manner of, for example, a catapult.

A "motor," as that term is employed herein in its broadest sense, is anything that creates work. For example, in some embodiments, a motor can be a combination of mechanical components that exhibits series elasticity, such as a link between a crossing member and either a proximal or distal member of a wearable device of the invention, and a suitable actuator.

Figure 3:
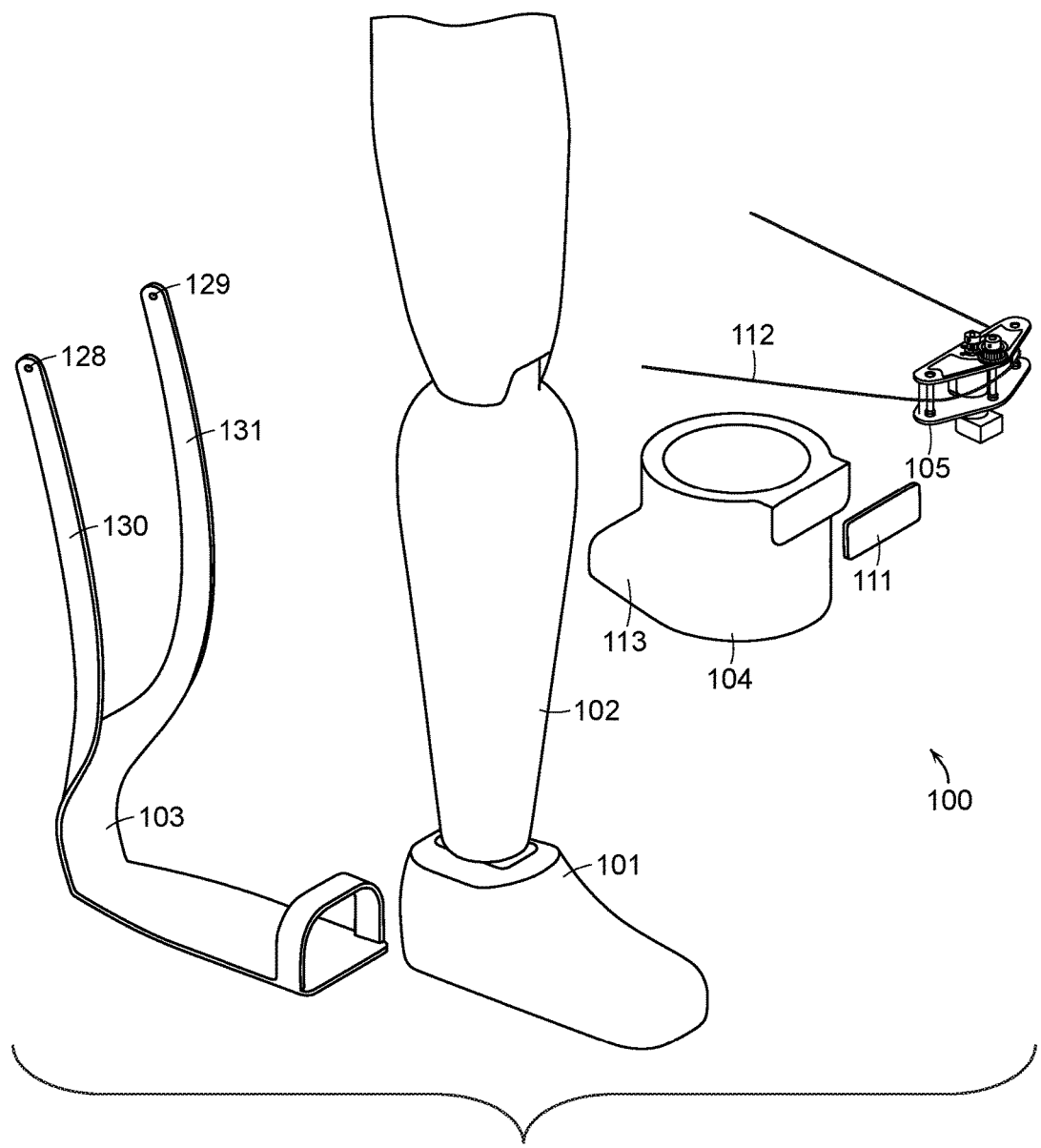
FIG. 3 is an exploded view of the embodiment shown in FIGS. 1, 2A and 2B.

Referring to FIGS. 1, 2A, 2B and 3, ankle exoskeleton 100 has distal member 103 connected to foot 101, and a proximal member 104 attached to shank 102. Ankle exoskeleton 100 has at least one crossing member, such as crossing members 130, 131. Proximal shank member 104 on ankle exoskeleton 100 does not pass through the virtual horizontal plane A (FIGS. 2A-2B). Distal foot component 103 has both medial crossing member 131 and lateral crossing member 130, with respective attachment points 129, 128 for the electric spool actuator cable 112 (FIG. 3). Force exerted by electric spool actuator 105 is measured with force sensor 111 placed between actuator body and proximal shank member 104. Proximal shank member 104 includes posterior protrusion 113 that guides crossing members 130, 131 and prevents them from snagging on the calf of shank 102.

Figure 6:
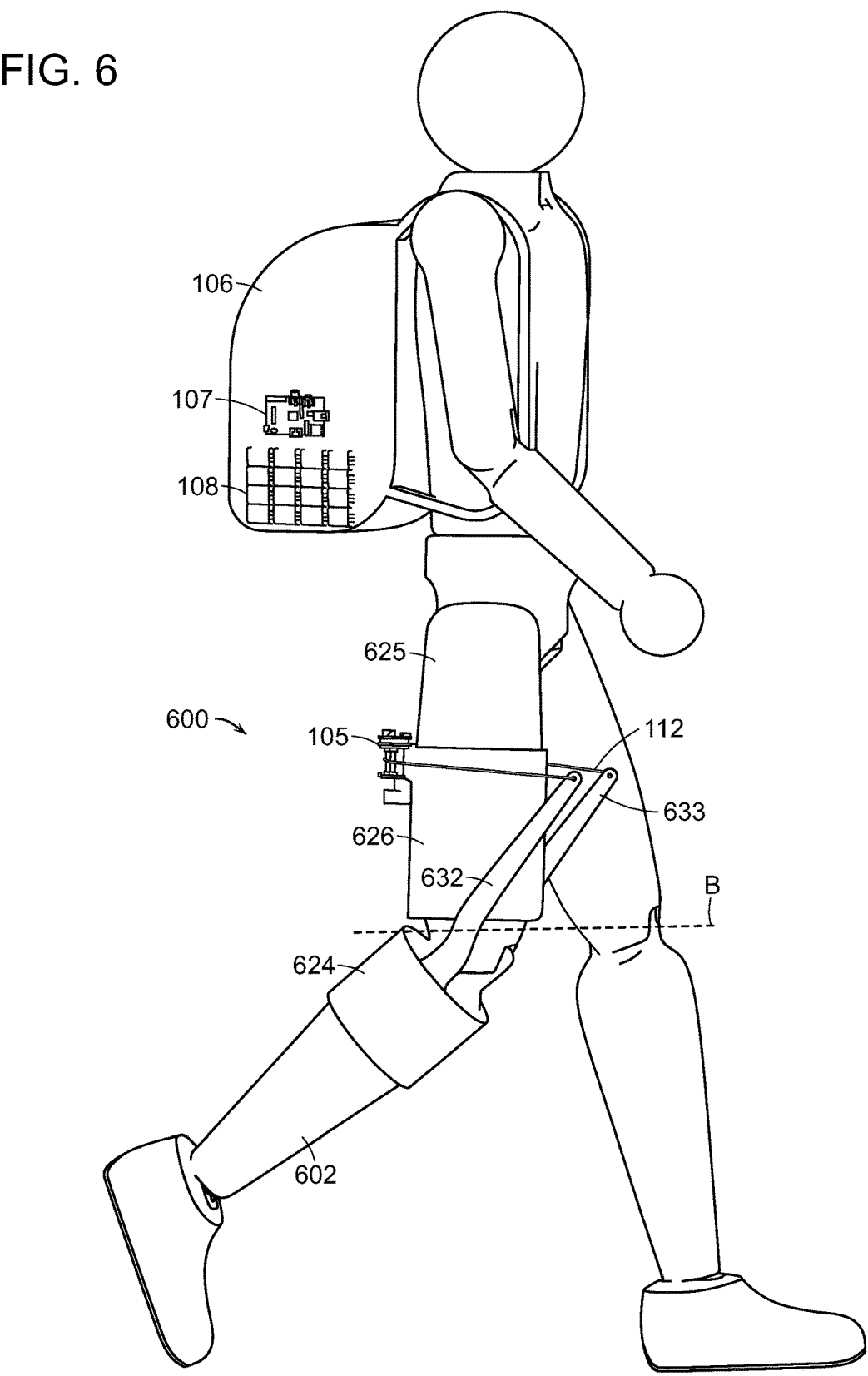
FIG. 6 is a full body view showing a knee exoskeleton embodiment of the invention.
Figure 7:
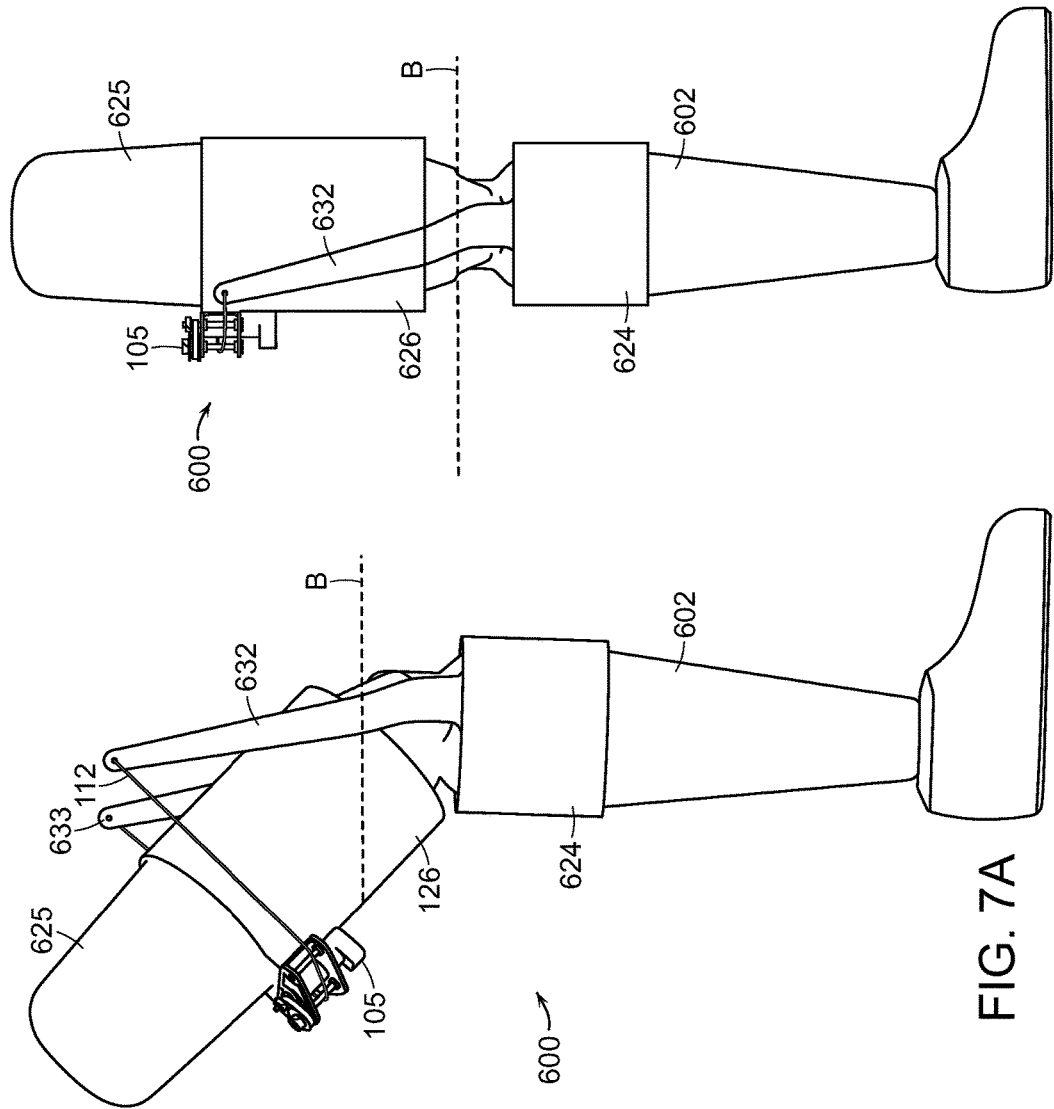
FIG. 7A is a side view of the knee exoskeleton of FIG. 6 during flexion.
FIG. 7B is a side view of the knee exoskeleton of FIG. 6 during extension.
Figure 8:
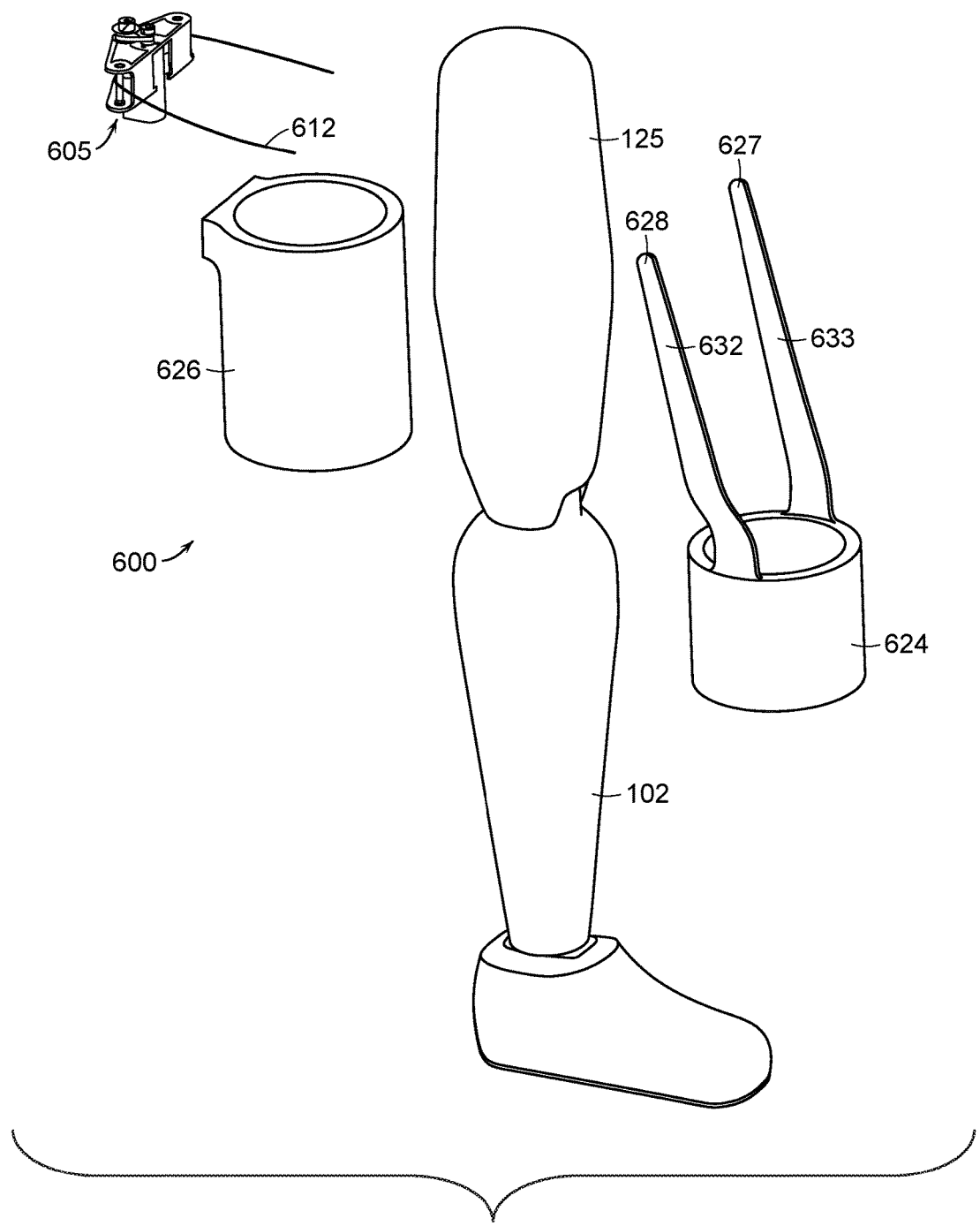
FIG. 8 is an exploded view of the knee exoskeleton of FIG. 6.

Knee exoskeleton 600, shown in FIGS. 6-8, includes distal member 624 connected to shank 602, and proximal member 626 attached to the thigh 625. Distal shin cuff 624 of knee exoskeleton 600 also has both a medial crossing member 633 and a lateral crossing member 632 with respective cable attachment points 627, 628, as shown in FIG. 8. Proximal thigh member 626 on knee exoskeleton 600 does not pass through the horizontal knee joint plane "B," shown in FIGS. 6 and 7.

Figure 9:
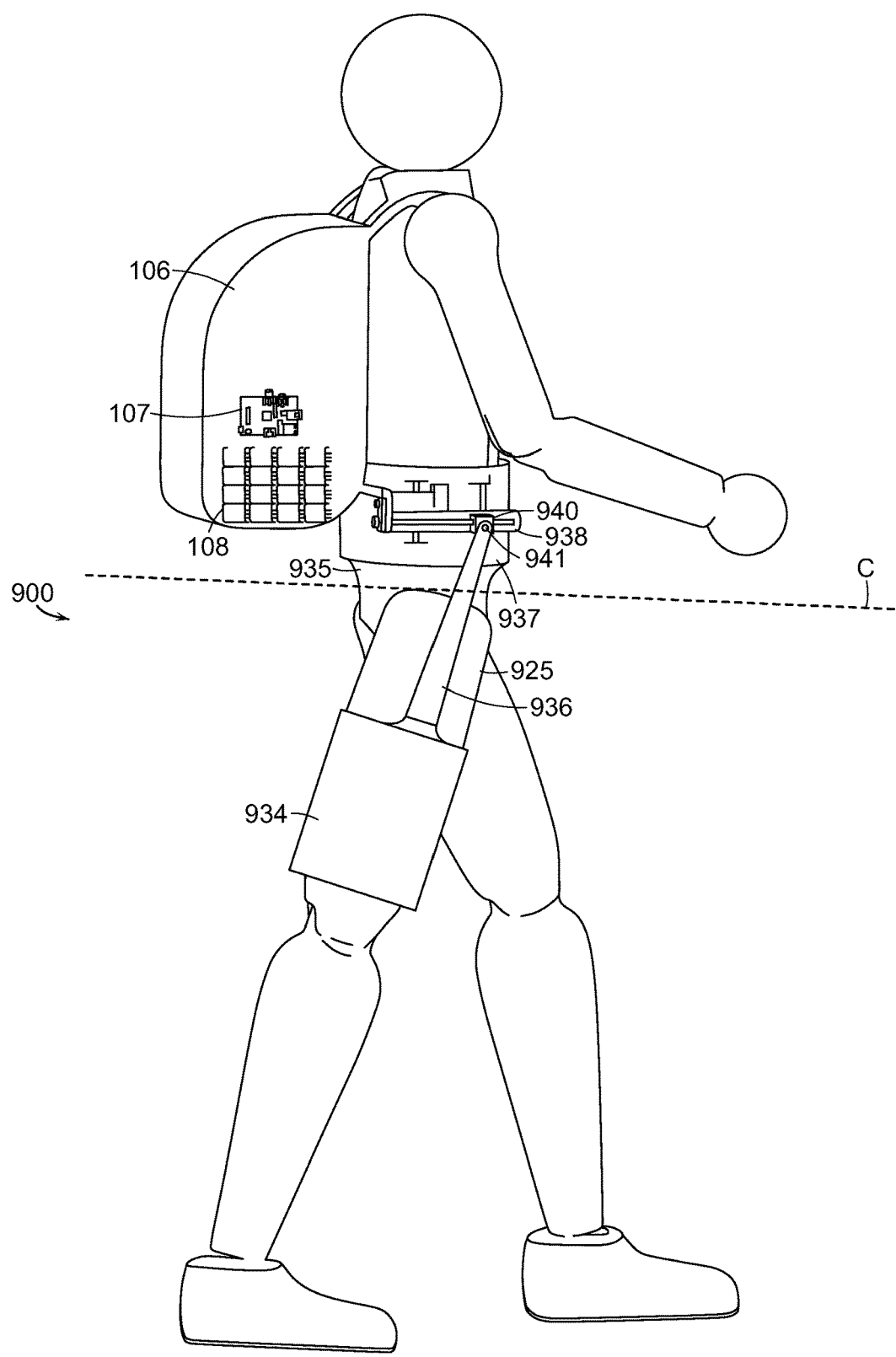
FIG. 9 is a perspective view of full body implementation of a hip exoskeleton of the invention.

As can be seen in FIG. 9, hip exoskeleton 900 has distal member 934 connected to thigh 625, and proximal member 937 attached to waist 935. Hip exoskeleton 900 also has lateral crossing member 936 attached to distal member 934. Proximal waist member 937 of hip exoskeleton 900 does not pass through horizontal hip joint plane "C." This exoskeleton includes ball screw actuator 938 to apply both flexion and extension moments about the hip of the individual wearing knee exoskeleton 900.

In each of the ankle, knee and hip exoskeletons described above, a moment is exerted about the respective ankle, knee and hip joints of the individual wearer by connecting a linear actuator to the crossing member and non-crossing member on the non-crossing side of each respective exoskeleton. For example, the depicted ankle and knee exoskeletons 100, 600, respectively, show spool actuator 105 spanning crossing members 130, 132 and 630, 632 and respective non-crossing members 104 and 626 on the proximal side of each joint. Cable 112 of spool actuator 105 links crossing members to non-crossing members and applies only a substantially linear force to the crossing members. Housing 115, shown in FIGS. 4 and 5, of spool actuator 105 is attached to proximal members 104, 626, (FIGS. 1 and 6, respectively), and the actuated cable end is attached to the proximal end of the distal members 128, 129, 627, 628 (FIGS. 3 and 8). Spool actuator 115 is discussed in more detail in Section 2.2, infra. Hip exoskeleton 900 (FIG. 9) includes a ball screw actuator 938 connected to crossing member 936 and the non-crossing member 937 on the proximal side of the hip joint. Connecting a linear actuator to the crossing member and non-crossing member on the non-crossing side of the joint enables a geometry in which shear forces on skin of the individual are reduced, and in which a large lever arm can be achieved, thereby increasing comfort and efficacy.

The stiffness and geometry of the crossing member(s) is important for flexibility and exoskeleton efficacy. The crossing member can either be flexible or rigid in both the sagittal and coronal planes of the individual wearing the device. Flexibility in the sagittal plane lends itself to a series-elastic actuator, and flexibility in the coronal plane increases joint flexibility. The crossing member can cross the joint in a variety of configurations. The depicted ankle and knee exoskeletons have two crossing members which extend from the distal member and cross the joint on the medial and lateral sides of the joint. Hip exoskeleton of FIGS. 9 and 10 has only one lateral crossing member, which crosses the hip joint. The crossing member could also span the joint on the posterior side or anterior side of the individual wearing the device.

There are a variety of suitable methods by which to physically attach the crossing and non-crossing members to the body of an individual. One possible method includes implementing a form-fitting cuff that relies only on friction and limb geometry to remain in place. The members can also be "glued" to the skin with a suitable bio-compatible adhesive, such as a bio-compatible adhesive known in the art. The members may also be tightened around the body with straps or buckles. The shape of the non-crossing member is tailored to prevent abrasion and collisions between the crossing member and the proximal body segment with which the crossing member is in contact. The depicted ankle exoskeleton of FIGS. 1-4 shows a proximal member with tapered back 113, which guides crossing members 130, 131 around shank 102 of the individual.

In general, actuator 105 can be located on either the distal member or the proximal member of the device. Usually, it is advantageous to place the actuator on the proximal member, to reduce the inertia of the device with respect to the individual's center of mass. This is advantageous from both a metabolic and comfort perspective.

Despite the aforementioned geometries implemented across a single joint of the lower extremity, the same principles can also be applied to bi-articular and multi joint devices. For example, the depicted ankle, knee and hip exoskeletons could be employed simultaneously. In one such implementation, the proximal member of the ankle exoskeleton can also operate as the distal member of the knee exoskeleton, and the proximal member of the knee exoskeleton can also operate as the distal member of the hip exoskeleton.

2.2 Actuator Design

The exoskeleton may require either a bidirectional actuator, an actuator that can apply forces in two directions, or a unidirectional actuator, which can only exert significant forces in one direction. A bidirectional actuator allows full control over the joint, but it also involves a greater amount of complexity. A unidirectional actuator is more limited in the forces it can exert, but it may be appropriate for joints, which only require large amounts of augmentation in one direction, such as the ankle.

Figure 4:
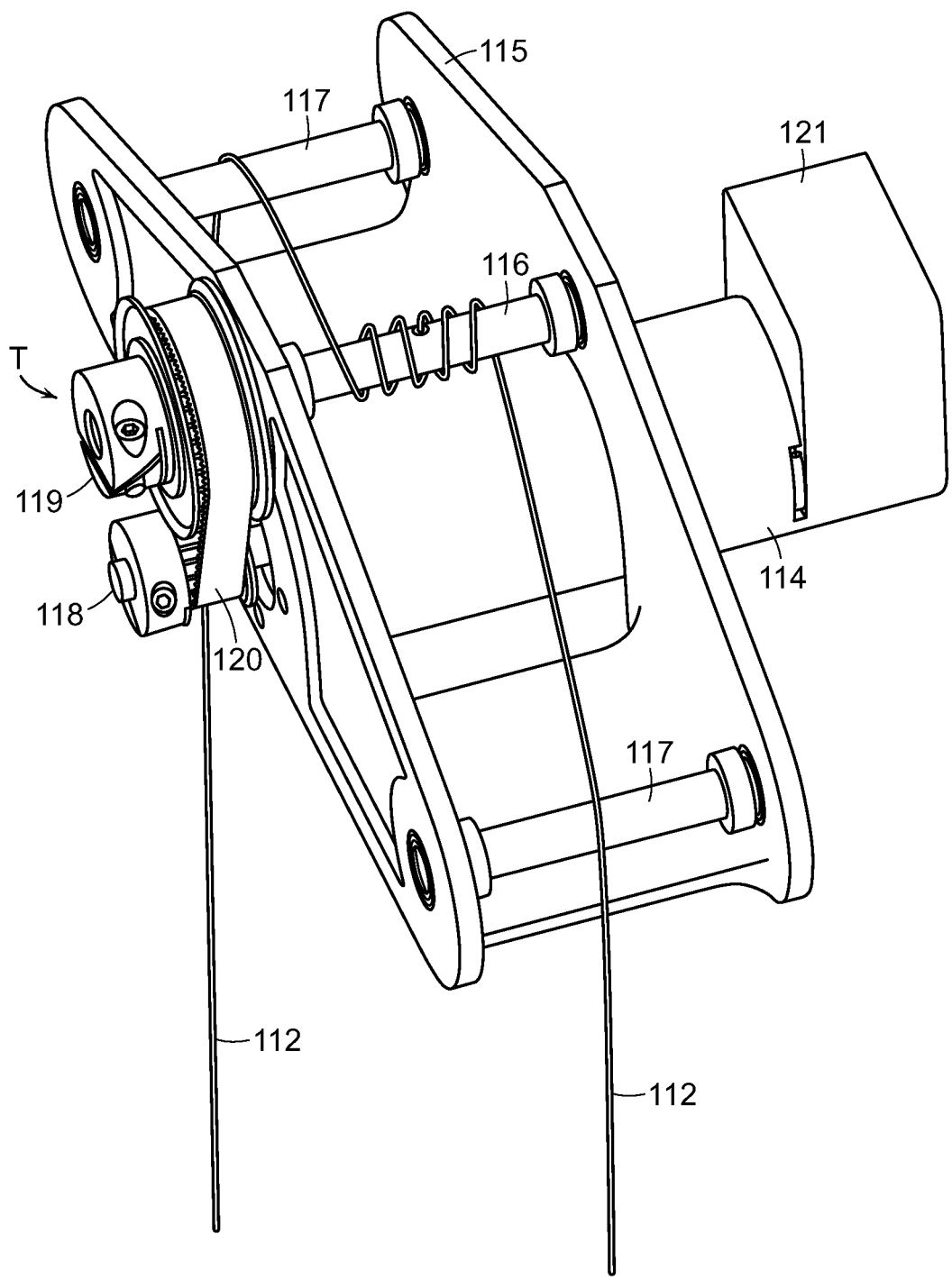
FIG. 4 is a perspective view of an electric spool actuator component of one embodiment of the invention.
Figure 5:
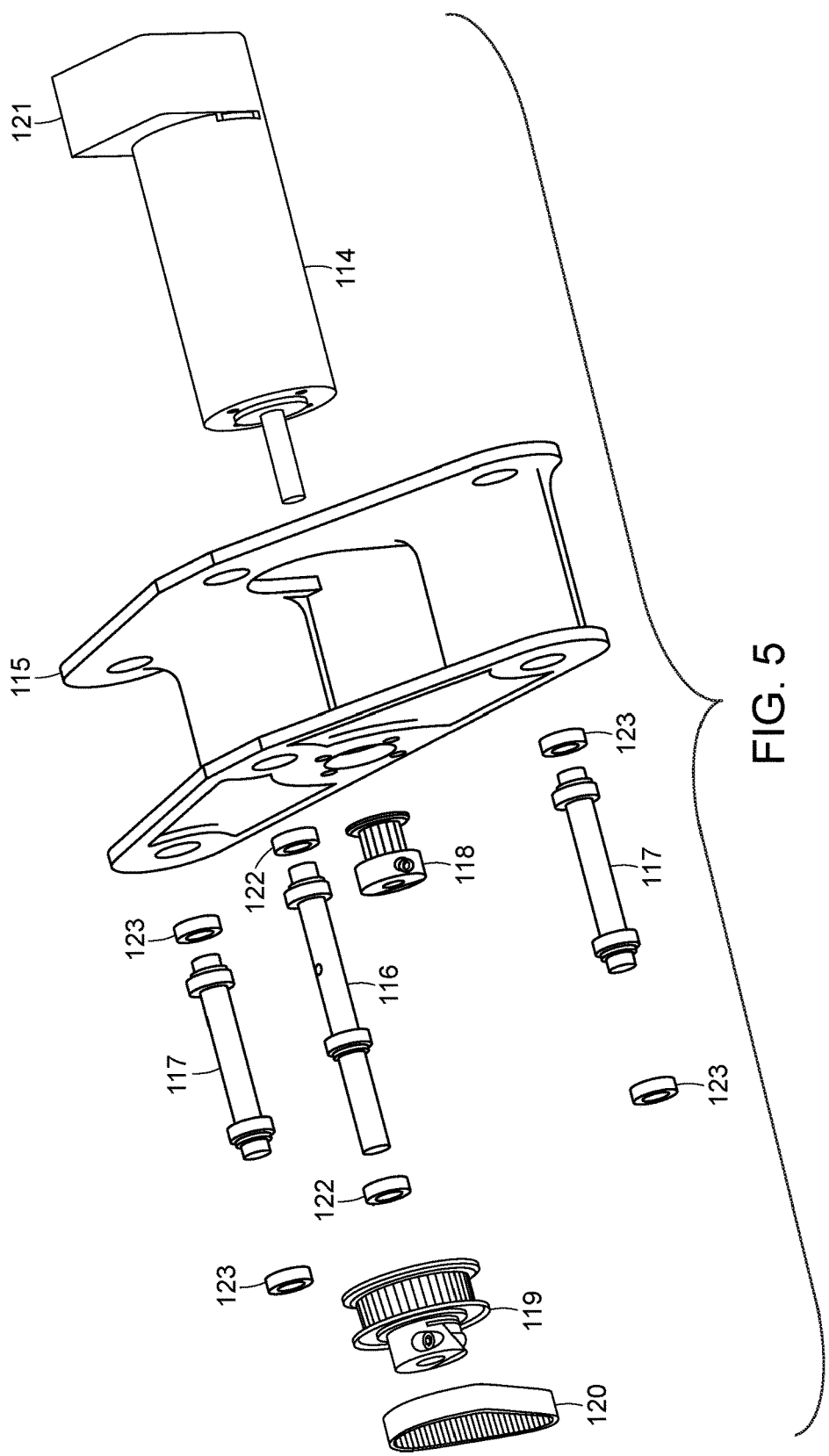
FIG. 5 is an exploded view of the electric spool actuator of FIG. 4.

Spool actuator 105, shown in FIGS. 4 and 5, employs electric rotational motor 114, such as a brushless motor, with belt transmission "T" to drive spool 116. Belt transmission T includes drive pulley 118, spool pulley 119 and belt 120. Spool 116 wraps cable element (e.g. string, cable, ribbon, etc.) 112, which exerts a force at the cable ends on, for example, proximal ends 128, 129 (FIG. 3) of crossing members 130, 131, respectively. Spool 116 runs on bearings 122 to reduce friction. Cable 112 is guided by pair of rollers 117 (FIG. 5), which run on bearings 123 to reduce friction. Spool actuator 105 is unidirectional, but the large lever arm of crossing members 130, 131 (FIG. 3) and the relatively small diameter of spool 116 (FIG. 5) provides efficient and compact transmission. The entire actuator system is housed in, for example, compact, low weight aluminum body such as housing 115 (FIGS. 4 and 5).

Ball screw actuator 938 shown, for example, in FIGS. 9 and 10, is a bidirectional electric actuator that employs rotational brushless electric motor 914 (FIG. 10) and belt drive transmission 917, including drive pulley 918, spool pulley 919 and belt 920, to drive ball screw 944 through ball nut 940. Ball screw actuator 938 can also be placed on linear bearings 939, 943 in order to reduce vertical shear on an individual's skin. Distal member, or thigh cuff 934 (FIG. 9), is attached at crossing member 936 to ball nut 940 via pin joint 941. Linear electric motors (not shown) could also be used as bidirectional actuators.

The high power density and inherent series elasticity of pneumatic actuators is advantageous in a device of the invention, such as an exoskeleton, prosthesis or orthosis of the invention. An air cylinder can be used as either a unidirectional or bidirectional actuator. Pressurized air is inherently elastic and can be exploited as a hardening series elastic element, where the stiffness increases with displacement. Inflatable bladders can also be employed as very low mass, high power, unidirectional actuators. Actuator valves can be used to control the flow of air through pneumatic actuators. The valves may, for example, be on/off or proportional valves. A pneumatic actuator, for example, could be powered passively, with a tank of compressed air or an onboard compressor. An onboard compressor could exploit the high energy density of liquid fuels such as hydrogen peroxide, gasoline or diesel.

2.3 Electronics and Controls

In order for the device of the invention to be autonomous, the energy source should, preferably, be carried onboard by the individual. The energy source can be directly attached to either the proximal member, the distal member, or a separate location, such as a backpack or waist pack 106, as shown in FIGS. 1, 6 and 9. The energy source can have both a high mass energy density and high volumetric energy density. The energy source may be one or a combination of the following: electric battery 108, pressurized air, combustible liquid (gas, diesel, hydrogen peroxide, propane), monopropellant (i.e. hydrogen peroxide), thermal cell, fuel cell or solar cell.

Onboard microcontroller 107 can use various sensors to autonomously control the exoskeleton. The sensors may include the following: at least one of a accelerometer, gyroscope, mechanical pressure sensor 111 (FIG. 3), at least one of a pneumatic pressure sensor, angle sensor, and encoder 121 (FIGS. 4 and 5), and at least one of a strain gauge, voltage sensor, current sensor, force sensitive resistor, EMG electrode, and thermistor (not shown). Microcontroller 107 (FIGS. 1, 6 and 9) employs these sensors to control the torque, position or velocity (or the relationship between these variables, known as impedance) of actuator 105.

Part II:

In another embodiment, the invention is directed to devices, such as a limb joint exoskeleton or assistive devices, that physically interface with an individual mismatching limb joint motion and mechanical interface motion in the same plane. In a specific embodiment, a device having multiple degrees-of-freedom (DOF) mechanism, and configurable to be mounted to an individual, includes: input component and output components that can be mounted on either side of a limb joint; a multiple DOF linkage system that allows torque transmitted from the input component to the output component; and a slider that connects the output link to the input link and allows the input component and the output component to rotate and translate with respect to each other in the same plane, so that the trajectory of variable instantaneous centers of the two components matches that of the biological joints.

2.4 Design Principle

In still another embodiment, the device of the invention includes a ground link that is fixed relative to either a distal end of a human femur or a proximal end of a human tibia. An input link having a first end and a second end is fixed to and rotates about a pivot defining an axis of rotation, wherein the pivot links the input link at the first end to the ground link. A coupler having a first end and a second end is pivotally mounted to the second end of the input link. An output link is fixed relative to the other of the distal end of the human femur or the proximal end of the human tibia and has a first end and a second end, the first end being pivotally mounted at the first end to the second end of the coupler. A sliding link is located between the ground link and the output link, whereby rotation of the human knee joint to which the device is secured will cause translation of an axis of rotation of the output link relative to the ground link to track two degrees of freedom of the human knee joint, wherein the human knee joint rotates in a sagittal plane about an axis that is normal to the sagittal plane but which moves relative to the axis of rotation of the pivot linking the first end of the input link to the ground link. In this embodiment, the sliding link includes a slot defined by the output link, wherein a protrusion from the ground link extends through the slot defined by the sliding link, the sliding link restricting movement of the axis of rotation of the output link to a line normal to an axis of rotation of the pivot.

One purpose of this invention is to modify the force distributions of an exoskeleton, orthosis or prosthesis on a limb. The intent is to alter the forces such that they are no longer parallel to the axis of the limb, but instead, perpendicular to the axis, whereby loading will be substantially more comfortable.

Another purpose of this invention is to transmit planetary torques from either active or passive devices to limbs without altering the normal biological joint motions. The intent is to apply torques to a limb by utilizing an unconstrained multiple DOF mechanism, thereby providing an adaptive trajectory of instantaneous centers of the device matching that of the biological joints.

The device of the present invention employs a geometric configuration that does not require artificial joints, therefore, making the device more comfortable and lighter. The comfort and weight of the device of the invention plays a large role in its ability to augment or rehabilitate the physical capabilities of an individual wearing the device.

The device of the invention can constrain the linkage system and set trajectories of instantaneous centers of the device in accordance with normal biological joint motions while the external sources apply torques to the joint at the same time. As a result, mismatch between limb joint motion and mechanical interface motion is largely avoided, as well as skin shear force, undesired slippage and sluggish interaction between the individual and the device.

The device of the invention can also act in the sagittal plane so that external sources can apply torques to joints of the individual without impeding rotation of the joint in the other planes, i.e., coronal or transverse planes. As a result, mismatch between biological ankle joint motion and mechanical interface motion is greatly avoided, as well as undesired large additional inertia added by the device worn by the individual.

In still another aspect of this invention, a force balance transmission is maintained in the sagittal plane of the individual so that external sources can apply torques to the biological joint in the sagittal plane without impeding rotation of the biological joint in the other two planes. The device of the invention also avoids significant skin shear force at the mechanical interface with the individual wearer. As a result, mismatch between ankle joint motion, for example, and mechanical interface motion is substantially avoided, as well as undesired large additional inertia added by the device of the invention.

Potential commercial applications of the present invention include enhanced human locomotory function. Specifically, enhancement may center on modification of ambulation of able-bodied persons or individuals with movement pathology. For use in able-bodied individuals, the invention can enhance locomotory function beyond what is otherwise physiologically possible. For example, physical enhancement could be employed to assist professional duties (such as military or civil service duties), athletic achievement, recreation, or other opportunities. Furthermore, gait dysfunction resulting from movement pathology, such as Parkinson's disease or knee osteoarthritis, or restoration of age-related reduced locomotory function could be treated or relieved by this invention. Each of these potential applications highlights the commercial possibilities associated with an exoskeleton with improved loading distribution.

Figure 11B:
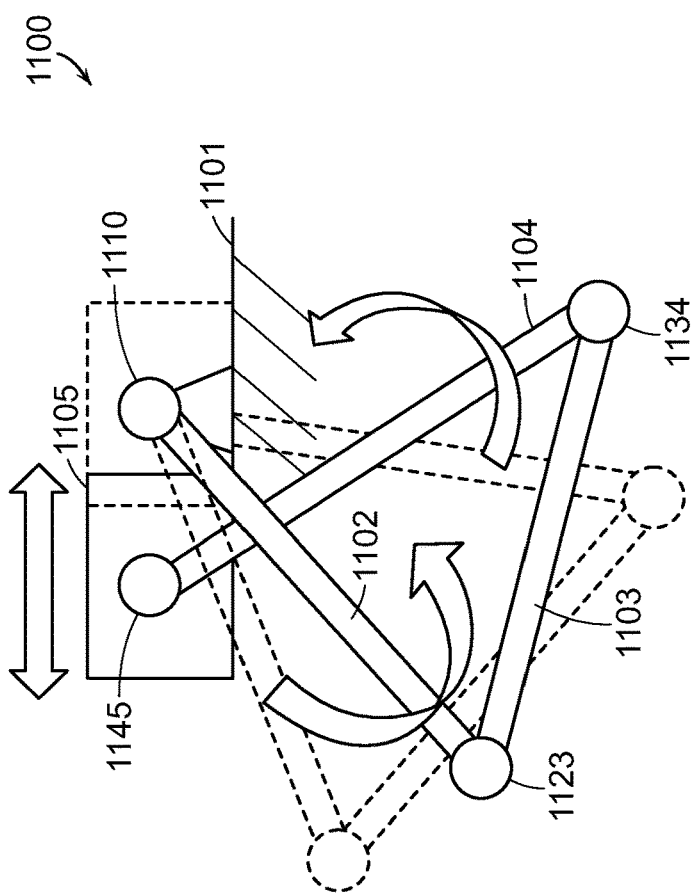
FIG. 11B is a topological representation of the two-DOF five-bar linkage system of the invention shown in FIG. 11A in a second position.
Figure 11A:
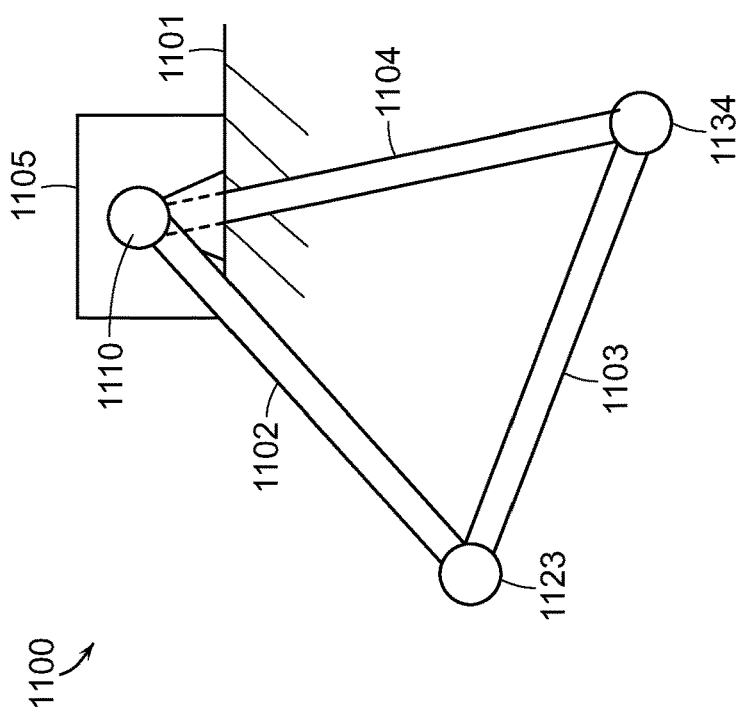
FIG. 11A is a topological representation of one embodiment of a two-DOF five-bar linkage system of the invention with an unfixed rotational axis in a first position.
Figure 11C:
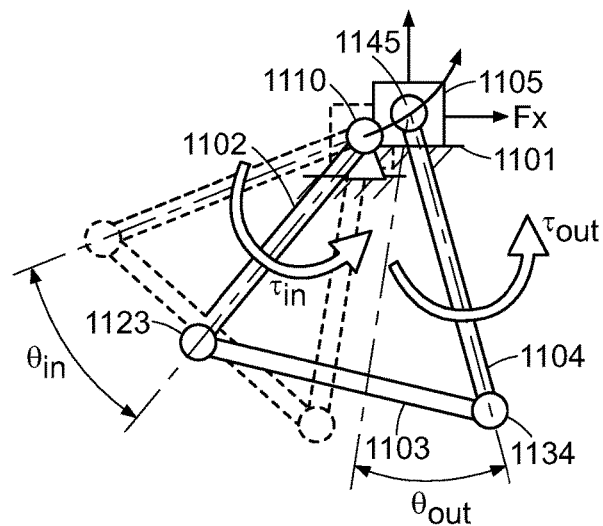
FIG. 11C is a topological representation of the two-DOF five-bar linkage system of the invention shown in FIG. 11A and a third position, wherein the mismatch between the artificial joint and the biological joint is different than that for the position shown in FIG. 11B.
Figures 11D, 11E:
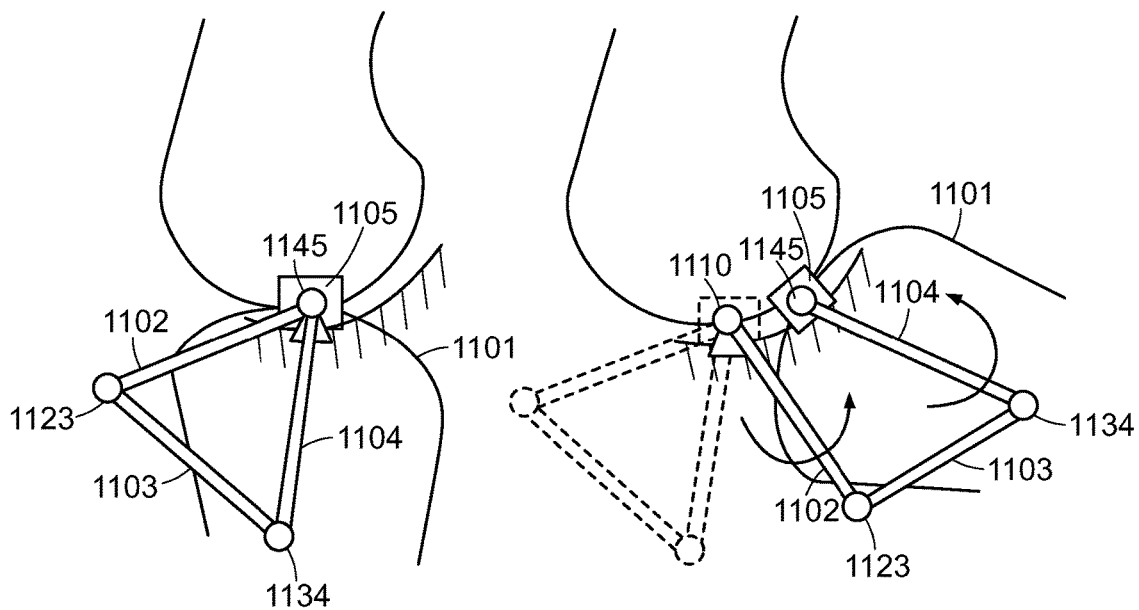
FIGS. 11D-E are topological representations of the two-DOF five bar linkage system in the third position and super imposed on a biological knee joint.

One embodiment of this invention is represented in FIGS. 11A through 11E as a topology of a two-DOF five-bar linkage system 1100 that provides a kinematic constraints that includes ground link 1101, input link 1102, coupler 1103, output link 1104, slider 1105, pivot joints 1110, 1123, 1134 and 1145, wherein connections are provided between ground link 1101 and input link 1102, between input link 1102 and coupler 1103, between coupler 1103 and output link 1104, and between output link 1104 and slider 1105, via pivot joints 1110, 1123, 1134 and 1145, respectively. Ground link 1101, as the proximal mount, is fixed to the main proximal component of the limb joint, and output link 1104, as the distal mount, is fixed to the main distal component of the joint. Input link 1102 exerts both flexion and extension moments about the joint. Slider 1105 translates with respect to ground link 1102 along a virtual or physical track at ground link 1101, which allows a virtual instantaneous center of input link 1102 and output link 1104. The track can be linear or curved. With an unfixed rotational axis, torques can still be applied to the limb from input link 1102 to output link 1104 via unconstrained two-DOF linkage system 1100. Tracking at ground link 1101 is not necessarily linear. FIGS. 11D-E are superimposed on a biological knee joint. See, Kuan, J.; Pasch, K. A.; Herr, H. M., "Design of a Knee Joint Mechanism that Adapts to Individual Physiology," Engineering in Medicine and Biology Society (EMBS), 2014, 36$^{th}$ Annual International Conference of the IEEE, pp. 2061-2064, 26-30 Aug. 2014, the teachings of which are incorporated herein by reference in their entirety.

Figure 12B:
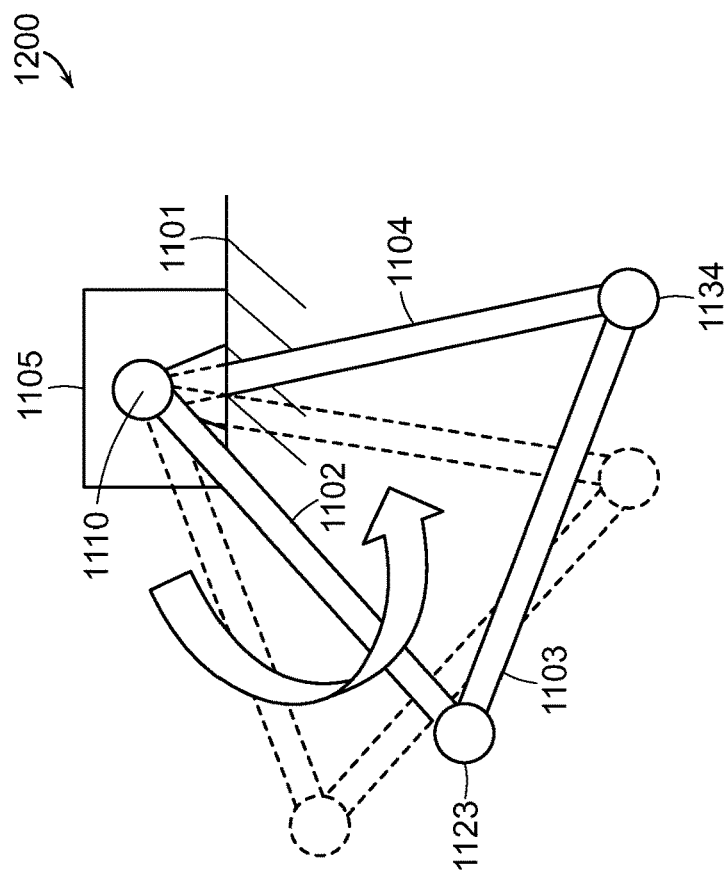
FIG. 12B is a topological representation of the two-DOF five-bar linkage system of the invention shown in FIG. 12A in a second position.
Figure 12A:
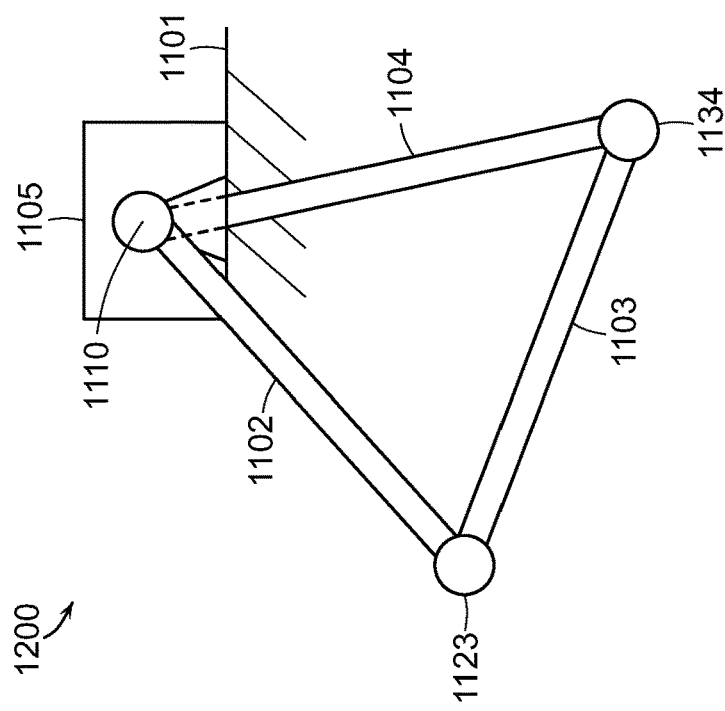
FIG. 12A is a topological representation of one embodiment of a two-DOF five-bar linkage system of the invention with a pure rotational constraint in a first position.
Figure 14:
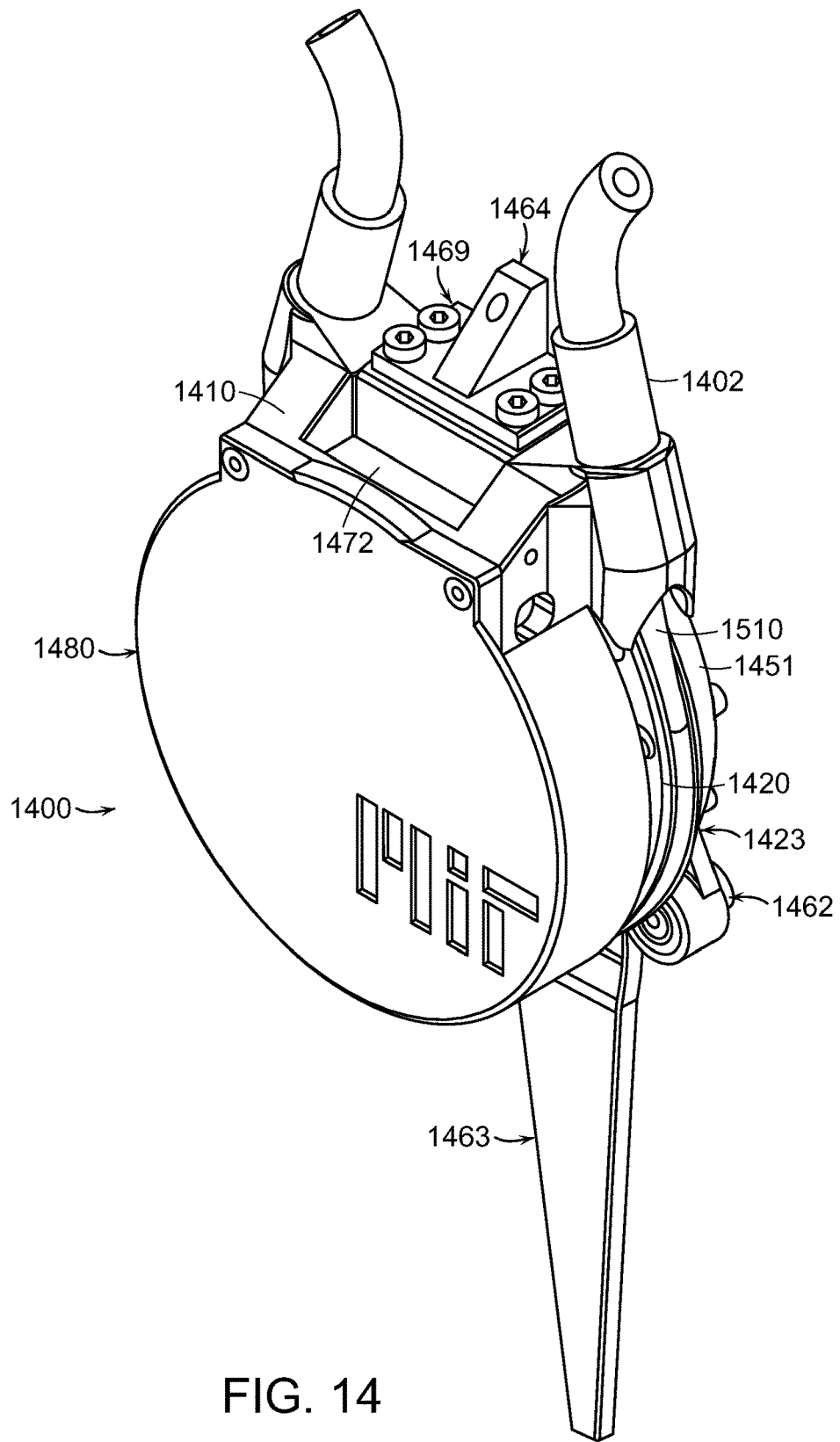
FIG. 14 is a perspective view of one specific embodiment of a joint mechanism of the invention.
Figure 15:
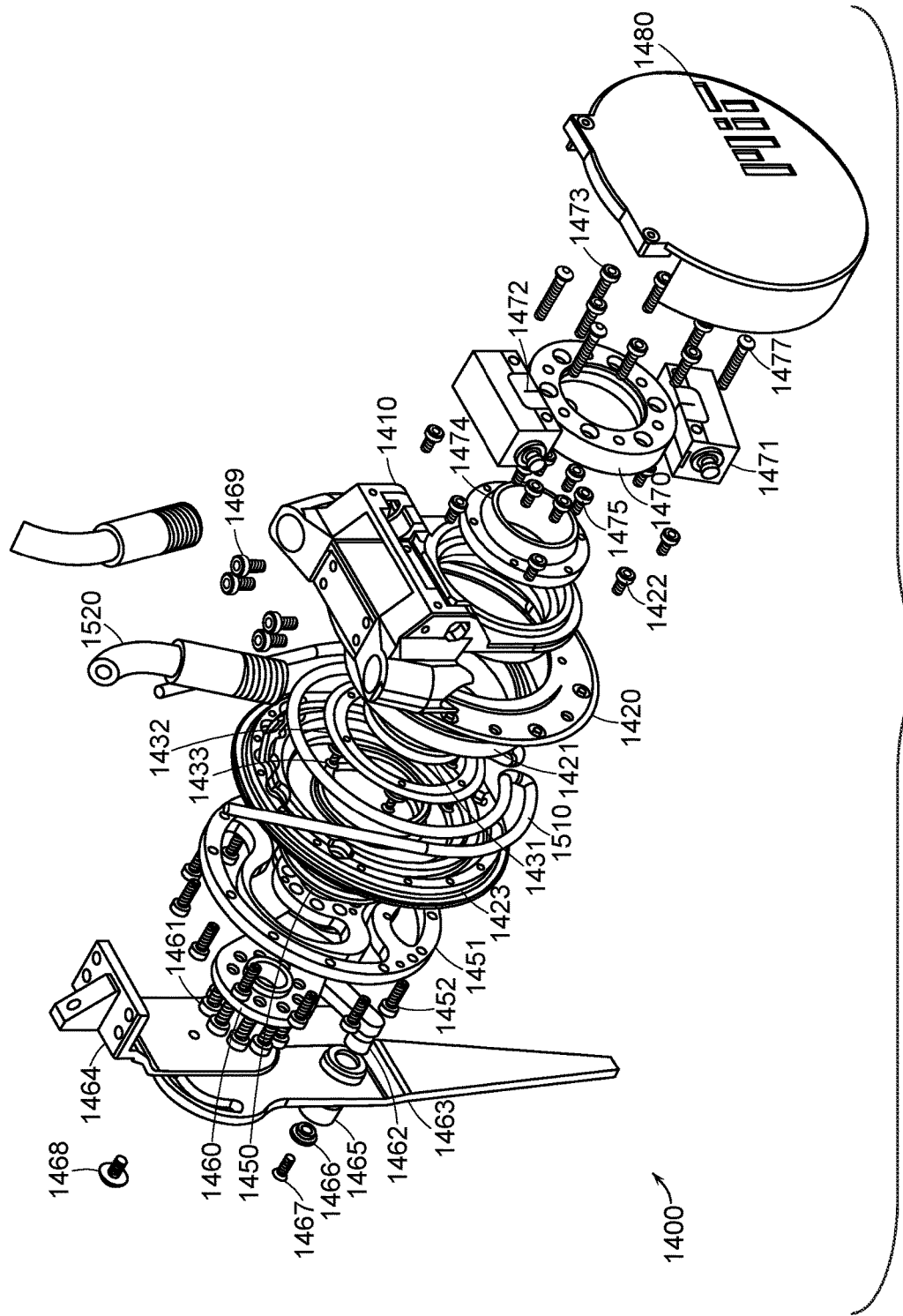
FIG. 15 is an exploded view of the joint mechanism of FIG. 14.
Figure 17B:
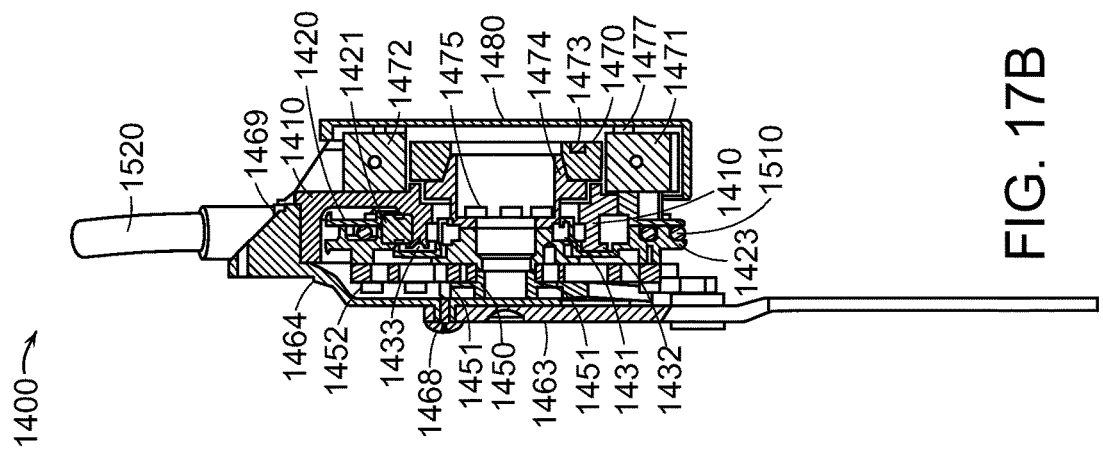
FIG. 17B is a cross sectional side view of the joint mechanism of FIG. 14.
Figure 17A:
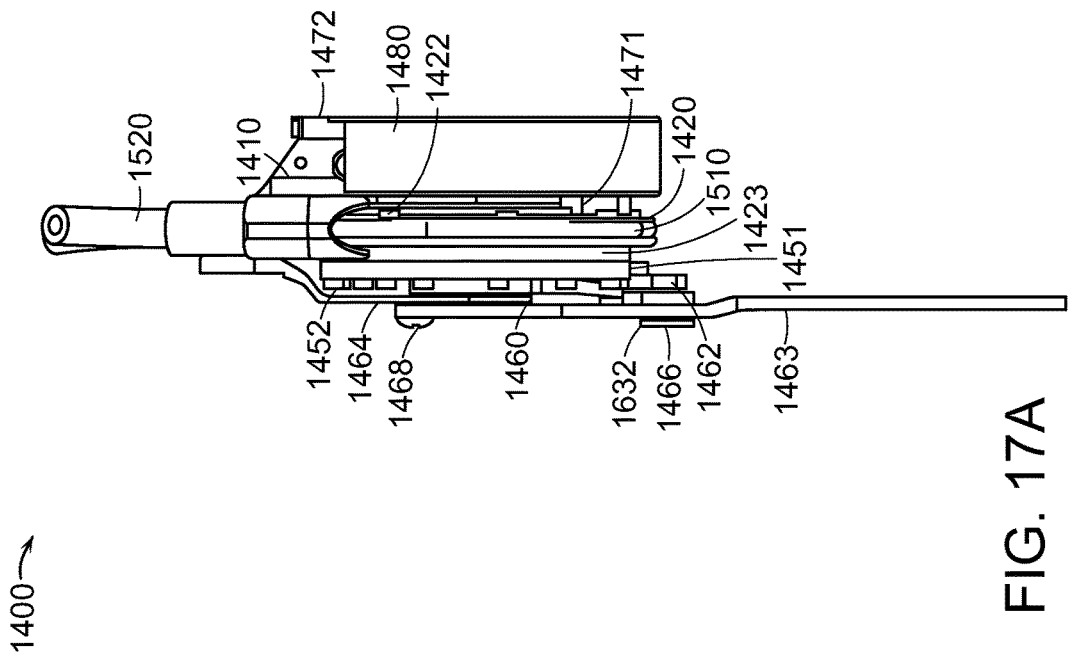
FIG. 17A is a side view of the joint mechanism of FIG. 14.
Figure 18A:
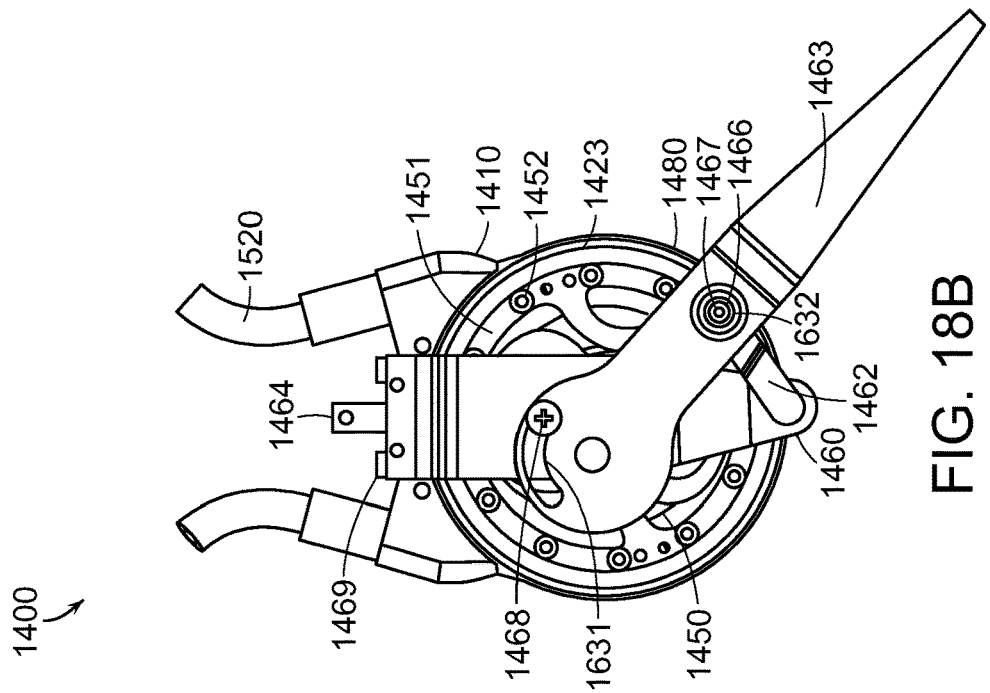
FIG. 18A is a back view of the joint mechanism of FIG. 14 in a first position.
Figure 18B:
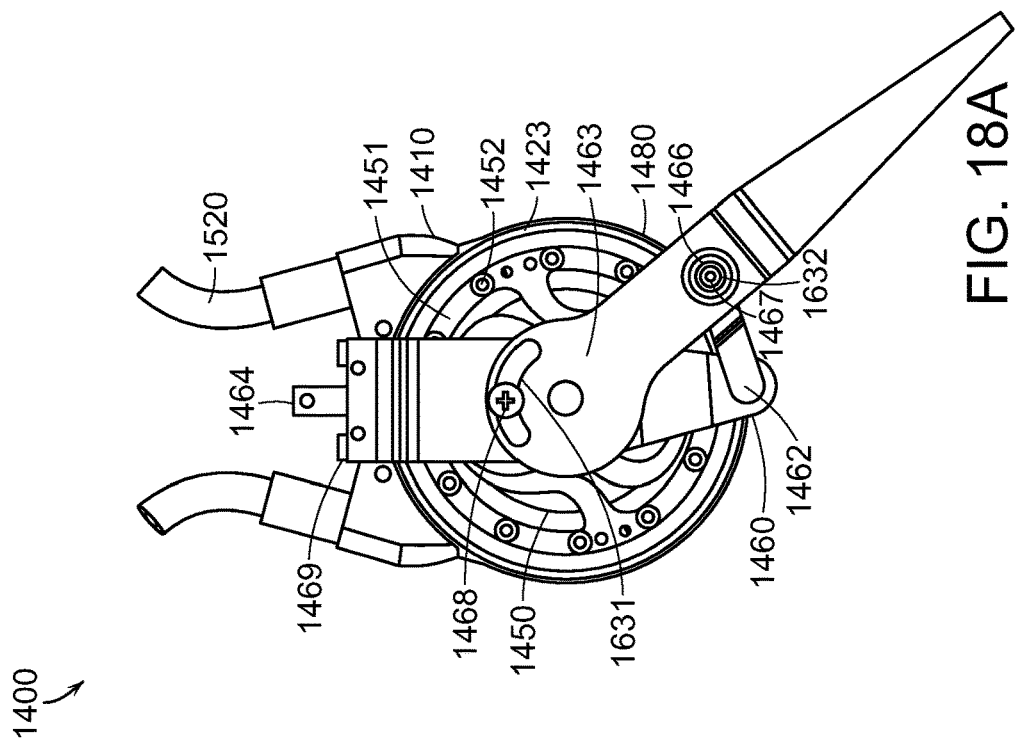
FIG. 18B is a back view of the joint mechanism of FIG. 14 in a second position of greater flexion than that of the first position shown in FIG. 18A.

Another embodiment of the two-DOF five-bar linkage system performs pure rotation where there is no mismatch between rotational axes of input to and output from a joint. FIGS. 12A and 12B are topological representation systems 1200 of the invention in first and second positions where the linkage system includes a pure rotational constraint. The lengths of input link 1102 and output link 1104 are set as the same, so that the linkage system performs pure rotation motion when the biological joint and pivot joint 1110 are coaxial. The biological joint regarded as a single one-DOF kinematic pair constrains the linkage system and sets the fixed rotational axis of the device in accordance with normal biological joint motion.

2.5 Mechanical Design

FIGS. 13A and 13B show a possible configuration of a two-DOF five-bar linkage system 1300 applied to knee joint 1302. Femur 1350 of knee joint 1302 is fixed to ground link 1304 and tibia 1360 is fixed to output link 1316. Ground pivot 1306 pivotally links ground link 1304 to input link 1308. Pivot 1310 pivotally links input link 1308 to coupler 1312. Coupler 1312, in turn, is pivotally linked to output link 1316 at pivot 1314. When knee joint 1302 is fully extended, virtual center of rotation A of output link 1316 is centered with ground pivot 1316, as illustrated in FIG. 13A. As can be seen in the transition from FIG. 13A to FIG. 13B, as knee joint 1302 rotates during flexion, input link 1308 can exert either a flexion or extension moment about knee joint 1302. Virtual center of rotation "A" of output link 1316 operates as slider 1105 does in transition from FIG. 11A to 11B, discussed above, and translates with respect to ground link 1304 along virtual track "B." Screw 1318, which is fixed to ground link 1304, slides within slot 1320 defined by output link 1316 as knee joint moves between positions represented in FIGS. 13A to 13B to thereby limit movement of virtual center of rotation A of output link 1316 to virtual track B of instantaneous centers of rotation consequent to flexion and extension of biological knee joint 1302. Torque can be applied to knee joint 1302 from input link 1308 to output link 1316 via the linkage system. Therefore, knee joint 1302 can rotate and translate in the same plane, and thereby provide an adaptive trajectory of instantaneous centers of rotation (between ground pivot 1306 and virtual center of rotation A) matching that of the tibia about the biological knee joint. The overall system can be considered a one-DOF five bar-linkage system. Namely, the knee joint can be regarded as a crank-rocked pair that constrains the linkage system and sets a specific trajectory of instantaneous centers of rotation of the device in accordance with normal knee joint motion. As a result, the mismatch between limb joint motion and mechanical interface motion can be avoided.

FIGS. 14, 15, 16, 17, and 18 show views of one specific embodiment of a joint mechanism that can be employed by the invention. As shown in FIGS. 14-18, joint mechanism 1400 includes cable conduit anchors 1402 and drum housing 1410, driven drum 1423 and torque sensor 1451, screw 1468, proximal mount 1464, output link 1463, and rotary optical encoder modules 1470, 1471, 1472. Proximal mount 1464 is fixed to the brace attached to the wearer's proximal limb while output link 1463 is fixed to the brace attached to the wearer's distal limb. Accommodated within track 1631 (FIG. 18), screw 1468 is fixed to proximal mount 1464 and acts like slider 1105 and ground link 1101 pair in the topology in FIG. 11, and causes output link 1463 to translate with respect to proximal mount 1464 along track 1631 of output link 1463, as a variable instantaneous center rotation between input link 1460 and output link 1463. Covered by bearing caps 1466 with screws 1467, two roller bearings 1465, mounted on sink hole 1632 of output link 1463 and input link 1460, are used to allow an individual to slightly move the limb forward or away from the midline of the body while providing torque flexing or extending the limb joint. With an unfixed rotational axis, torques can still be applied to the limb from input link 1460 to output link 1463 via the unconstrained two-DOF linkage system. Joint mechanism 1400, therefore, provides specific planar constraints when there is a mismatch between rotational axes of a limb joint, such as a biological knee joint, and as a mechanical interface. As can be seen in FIG. 18A, the mechanism provides pure rotational constraints when there is no mismatch between limb joint and mechanical interface. As can be seen in FIG. 18B, the mechanism provides specific planar constraints when there is a mismatch between the rotational axes of the limb joint and the mechanical interface.

As shown in the embodiment of the invention shown in FIGS. 14-18, driven drum 1423 is actuated by inner cable 1510 in a pull-pull configuration, driving the limb joint via torque sensor 1451 and output link 1463 with small friction due to four-point contact bearing 1421 incorporated in drum housing 1410. Driven drum cap 1420 is fixed to driven drum 1423 by screws 1422 and bearing cap 1432 is fixed to drum housing 1410 by screws 1433. They are used to set a constraint on the linear motions between bearing 1421 and driven drum 1423. A four-point contact bearing 1421 can also resist high radial force caused by cable tension.

A torque sensor includes a series rotatory spring 1451 connecting driven drum 1423 to input link 1460. Inner part of spring 1451 is secured to input link 1460 and torque sensor mount 1450 by screws 1461. Rotatory encoder disk 1470 is mounted on encoder disk mount 1474 by screws 1473. Encoder disk mount 1474 is secured on torque sensor mount 1450 by screws 1475. Four-point contact bearing 1431 is used between torque sensor mount 1450, encoder disk mount 1474 and driven drum 1423 to provide only relative rotational motions between driven drum 1423 and spring 1451. Rotatory encoder disk 1470, encoder disk mount 1474, torque sensor mount 1450, spring 1451, and output link 1460 rotate simultaneously. Encoder reader 1472, mounted on drum housing 1410 by screws 1477, can measure the relative rotational angles between drum housing 1410 and the input link 1460. Outer part of spring 1451 is secured on driven drum 1423 by screws 1452. Encoder reader 1471, mounted on driven drum cap 1420 by screws 1477, can measure the relative rotational angles between the input end and the output end of spring 1451, and thus is used to measure the output torque. Cover 1480 is used to protect encoder readers 1471, 1472 and encoder disk 1470. Using a digital encoder to measure the strain caused by output torque reduces the effect of the electromagnetic field. The torque sensor and the encoder can collect the joint state as the feedback information for both real-time control and subsequent analyses. For instance, the control scheme mentioned in part I can be used to control the mechanical joint.

In still another embodiment the invention is directed to an ankle joint exoskeleton or assistive device that physically interfaces with an individual without adding significant inertia on human legs, while wherein for example, mismatch between ankle joint motion and mechanical interface motion is in the same plane, and avoiding skin shear force. In one specific embodiment, three-DOF mechanism, configurable to be mounted to an individual's shank and foot, has a force balance transmission that allows an ankle joint to perform external-internal rotation and inversion-eversion rotation while applying a torque in the sagittal plane, so the attached biological ankle joint can maintain a normal gait.

2.6 Mechanical Design

In another embodiment, the crossing member is not rigid. In this embodiment, the link includes a strut extending from the proximal member to the distal member, whereby the crossing member and the strut span the axis about which the distal member rotates. In a specific embodiment, the strut is constrained at the proximal member normally and laterally to a major longitudinal axis of the crossing member extending from the proximal number to the distal member, wherein the strut is not restricted along the major longitudinal axis of the crossing member. In this embodiment, the link further includes at least one roller at the proximal member that constrains the strut normally and laterally. The link includes at least one pair of rollers in opposition to each other, wherein the strut is normally constrained between the pair of rollers. The strut can be curved at the pair of rollers, whereby shear force between the strut and pair of rollers during rotation of the distal member of the axis spanned by the crossing member and the strut is less than it would be if the strut were straight at the pair of rollers. The strut includes a guide tube at the pair of rollers, wherein the crossing member extends through the guide tube. In one embodiment, the device includes a pair of crossing members and a pair of struts. In a specific embodiment, the struts are essentially straight between the rollers and the distal member. In one particular embodiment, at least one of the struts deflects during eversion and inversion of the human foot secured to the distal member and a human calf secured to the proximal member. Typically, the struts are rigid. In one embodiment, the struts are curved, whereby the struts operate as series springs during a normal walking cycle of human foot secured to the distal member and the human calf secured to the proximal member.

In one embodiment, the link further includes a winch actuator assembly attached to a proximal end of the pair of crossing members, whereby actuation of the link will cause retraction of the crossing member, which causes rotation of the distal member and plantar flexion of the human foot secured to the distal member about a human ankle joint. In another embodiment, the pair of crossing members is fixed to a proximal end of the distal member. A second pair of crossing members can be fixed to a distal end of the distant member. In one specific embodiment, the link further includes a second winch actuator assembly attached to a proximal end of the second pair of crossing members, whereby selective actuation of the link causes retraction of the second pair of crossing members, which causes rotation of the distal member and dorsiflexion of the human foot secured to the distal member about the human ankle joint. In a specific embodiment, the distal members are configured to fit the human calf. In this embodiment, the proximal member can be configured to fit the human thigh. In one embodiment, the crossing member extends proximally from the distal member, and the link extends between the proximal member and a proximal end of the crossing member, whereby actuation of the link will cause extension of a human leg secured to the proximal and distal members. Alternatively, the crossing member extends distally from the proximal member and the link extends between a distal end of the crossing member and the distal member, whereby actuation of a link will cause extension of the human leg secured to the proximal and distal members.

In another embodiment, the proximal member is configured to fit a human waist. In this embodiment, the distal member is configured to fit a human thigh. Preferably, the crossing member extends proximally from the distal member. In one such embodiment, the link includes a bidirectional actuator, whereby actuation of the link will rotate the distal member and a human thigh secured to the distal member about a hip joint of a human wearing the device. In one embodiment, the bidirectional actuator is a ball screw actuator.

Figure 19A:
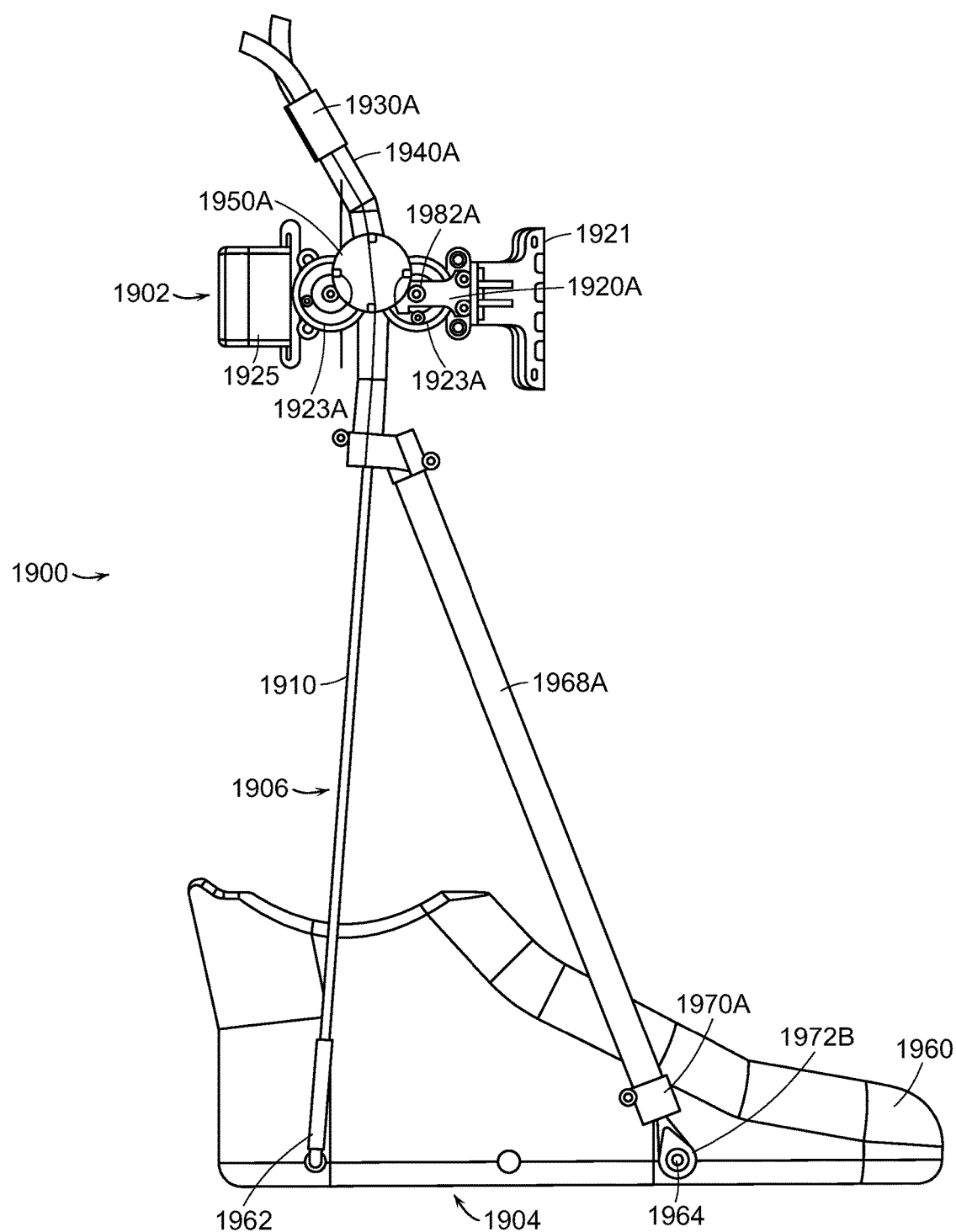
FIG. 19A is a profile view of another embodiment of an ankle joint mechanism of the invention.
Figure 19B:
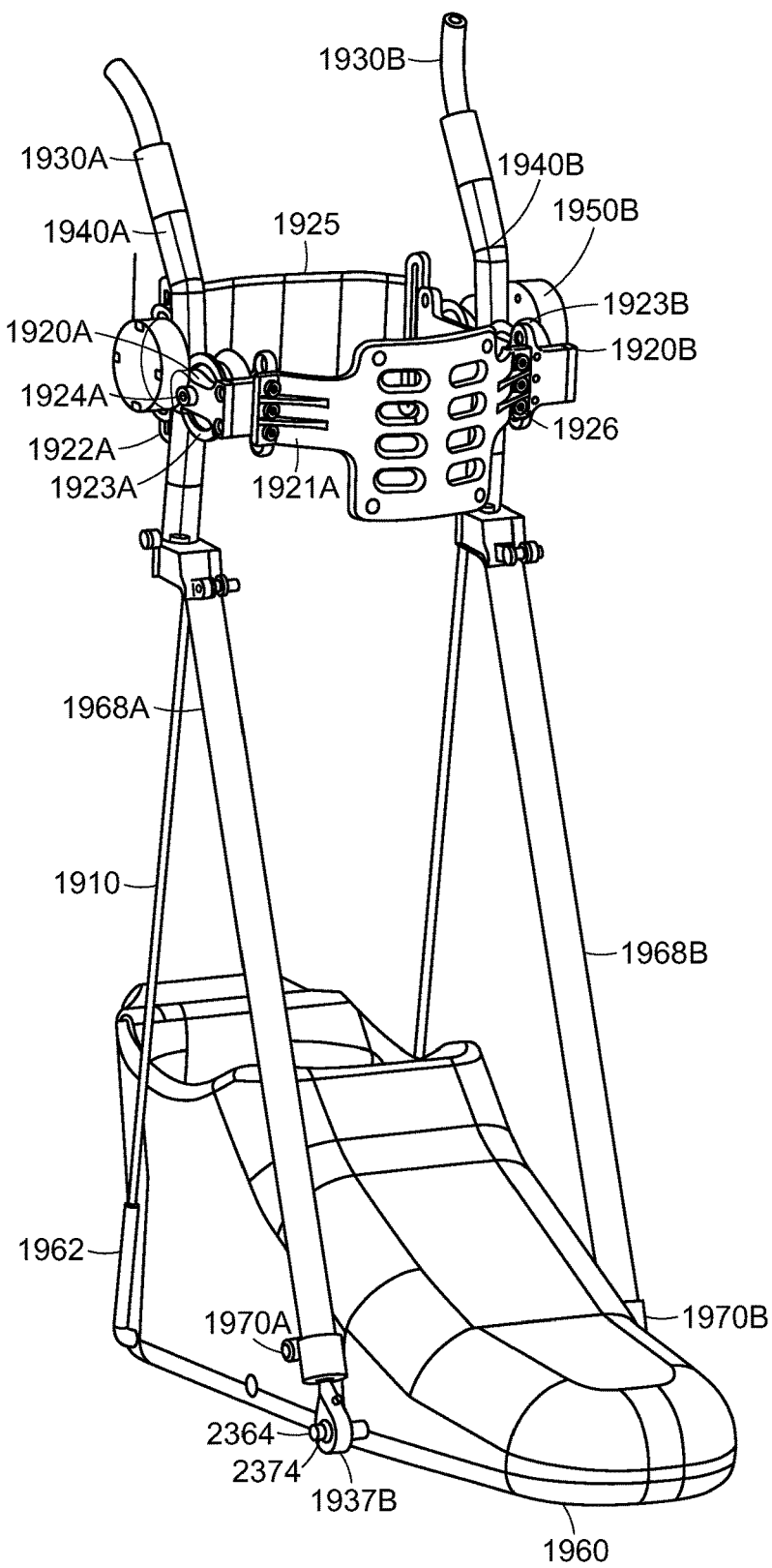
FIG. 19B is a perspective view of the ankle joint mechanism of FIG. 19A.

As shown in FIGS. 19A and 19B, an ankle joint device 1900 includes shank guard component 1902 mounted on an anterior shank of an individual, output component 1904 configured to fit the individual's foot, and transmission component 1906, or crossing member, transmitting torque from an input component such as a motor and coil (not shown) linked to cord 1910, which is linked to output component 1904. Shank guard component 1902 includes shank brace 1921, two pairs of rollers 1923A, 1923B, two roller mounts 1920A, 1920B, fastening strap 1925, and two position sensors 1950A, 1950B. Output component 1904 includes shoe 1960, nylon tube 1962 and axle 1964. The transmission component 1906 includes a pair of curved guide tubes 1940A, 1940B, two cable conduits 1930A, 1930B, two output rods 1968A, 1968B, two rod end clamps 1970A, 1970B, and cord 1910.

Roller mounts 1920A, 1920B are fixed to the each side of brace 1921, and fastening strap 1925 wraps itself around the loops of two roller mounts 1920A, 1920B, forming a loop that an individual can put on as a conventional shank guard. After putting it on, the individual can adjust fastening strap 1925 to make a proper fitting. Rear rollers of roller pairs 1923A and 1923B are fixed to pins on roller mounts 1920A, 1920B, and two moving pins 1924A, 1924B that slide along the slots on roller mounts 1920A, 1920B confine the movements of the front rollers along the roller mounts 1920A, 1920B, allowing some mismatched alignments of curved guide tubes 1920A, 1920B and rollers 1923A, 1923B due to contact area changes.

One end of output rod 1968A is clamped to one end of curved guide tube 1940A and the other end is clamped to rod end clamp 1970A by cap screws. One end of output rod 1968B is clamped to one end of curved guide tube 1940B and the other end is clamped to rod end clamp 2320B by cap screws, as well. Spherical bearing rods 1972A, 1972B are screwed to rod end clamps 1970A, 1970B, and attached to the each end of axle 1964 through the front outsole of boot 1960 via clips 1974A, 1974B, respectively. Screws and a taped axle can be used to secure rod end clamps 1970A, 1970B to the axle without using clips 1974A, 1974B. Spherical bearing rods 1972A, 1972B transmit the force generated by cable conduits 1930A, 1930B from two output rods 1968A, 1968B, to shoe 1960 and allow the ankle to voluntarily perform eversion, inversion, and external and internal rotation. The other ends of curved guide tubes 1940A, 1940B are fixed to the end pieces of cable conduits 1930A, 1930B, respectively. On each side of the shank guard component, roller mounts 1920A, 1920B confine pairs of rollers 1923A, 1923B, respectively, providing normal and lateral forces to constrain each curved guide tubes 1940A, 1940B in the sagittal plane while still allowing the curved guide tubes 1940A, 1940B to freely move upward and downward through a full range of motion.

Figure 20:
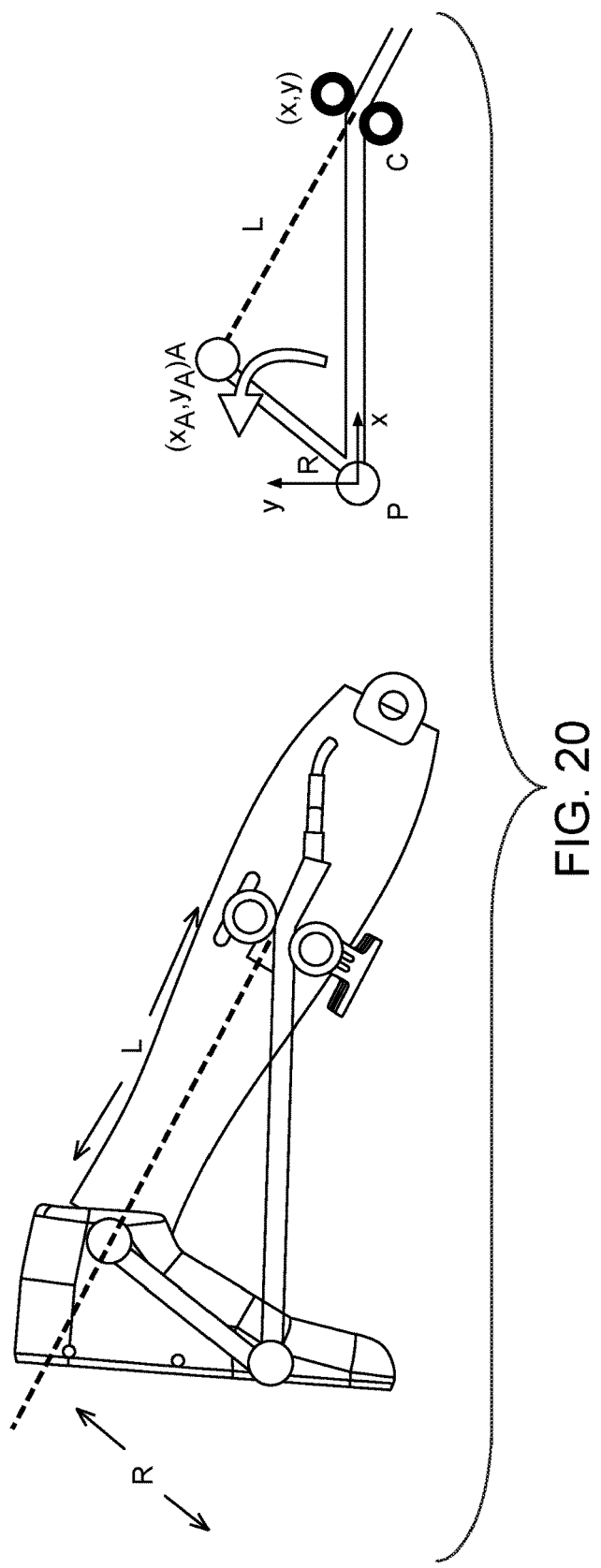
FIG. 20 is a schematic representation of optimal shape derivation in one embodiment of the invention. The origin of the body-fixed coordinate system coincides with the axle on lower left in the picture. The output rod defined as Ground link is horizontal. The foot link is defined from origin to the ankle A. The shank link is from (x,y) to the curly extension of the guided tube. R is the length of the foot link and L is the length of the shank link.

In order to achieve zero skin shear, instantaneous velocities of curved guided tubes 1940A, 1940B through the full range of motion shall be parallel to the shank, namely, curved guided tubes 1940A, 1940B contacting the same tangent points of rollers 1923A, 1923B all the time. With reference to FIG. 20, given the predefined parameters length of foot link R and radius of shank link L, the equations can be defined as:

Differential equation:

$$\frac{dy}{dx} = \frac{y - y_a}{x - x_a} \qquad (1)$$

Subject to the constraints:

$$x_2^\alpha + y_\alpha^2 = R^2 \quad (2)$$

$$(x-x_A)^2 + (y-y_A)^2 = L^2 \quad (3)$$

where R is the length of the foot from the ankle to the axle 806, L is the length of the shank from the ankle to the rollers, (x, y) is where the rollers contact the curved guided tube, and ($x_A$, $y_A$) is the location of the ankle joint, all with respect to the curved guided tube. Solving the differential equation (1) subject to the algebraic constraints (2), (3) with the coordinate defined in FIG. 20, the optimal geometry of the curved guide tubes 1940A, 1940B can be derived so that no shear force would be generated between the rollers 1923A, 1923B and curved guide tubes 1940A, 1940B, thus eliminating skin shears.

Alternative ways of accomplishing the same motion accompanied by zero shear force, for example, include attaching rollers to the guided bar that can move up and down a designed curved track on the roller mounts, letting the point of horizontal force move up and down the shank; and variation of a Chebyshev straight line mechanism that has two trusses or cords connecting two points of the guided tube to two points of the shank guard can also achieve the same function with designed parameters.

Two ends of cord 1910 connect to the input source via two cable conduits 1930A, 1930B. In sequence, cord 1910 runs from an input source via cable conduit 1930A, through the hole of guide tube 1940A, nylon tube 1962 anchored in the boot heel, other guide tube 1940B, and back to the input source via other cable conduit 1930B. The input source can pull cord 1910, and then output rods 1968A, 1968B to transmit the force from the input source to shoe 1960 and then apply the torque to the ankle joint in the sagittal plane. Nylon tube 1962 allows the cord 1910 to equally distribute an input force to the each side of the shoe 1960 even when the ankle performs eversion and inversion rotation. Two position sensors 1950A, 1950B are used to measure the displacement of guide tubes 1940A, 1940B so as to measure angles of the plantar-dorsal flexion and inversion-eversion. The linear potentiometers and encoders can also be used to measure the displacement of guided tubes 1940A, 1940B. Moreover, the ankle angle can be directly measured by using an electrogoniometer or inertial measurement units.

The force/torque sensing can be achieved by using in-line cable tension sensors attached to cord 1910, conduit housing compression sensors attached to curved guided tube 1920A, 1920B, strain gauges attached to roller mounts 1920A, 1920B or the output rods 1968A, 1968B, built-in spherical bearing force sensors, or springs, for example. The output rods 1968A, 1968B can be curved or slender, so they act like series springs, increasing the force controllability and the level of safety as well as acting a force-sensing device. To reduce the ground reaction force and share loading with foot arches, an arch spring or strut can also be introduced to replace rigid axle 1964. It can also act as a force sensing mechanism by measuring deformation and using Hook's law. Referring back to FIGS. 19A and 19B, simple struts that attach near ankles with side bars or plates on the shoe 1960 can also be used to reinforce the force transmission of the device.

In this embodiment, the device can only apply unidirectional torque to ankles, but bidirectional torque can be applied to ankles by attaching another cord running from the actuation source to the front outsole of the shoe 1960 or to the designed structure fixed to the shoe 1960. Another way is to replace cord 1910 and cable conduits 1930A, 1930B with a flexible transmission and two rigid members, so the device can be operated at a pull-push configuration, actuating ankles in the both plantar flexion and dorsiflexion directions.

The range of motion of the device is set to allow a normal wearer to walk or run at self-selected speed. The device on each leg is very lightweight compared to the existing devices, but it is capable of providing large torques via cable driven actuation or an onboard motor because of a large moment arm from the nylon tube anchor point to the axle. In practice, for the simple gait detection, a foot switch can be used to determinate when to apply torque to the ankle to reduce the metabolic cost. The invention can be further modified to act as a passive device without any power or as a quasi-passive device that requires little power. The module can further be used as a measurement tool for estimating biological properties of an ankle.

Part III:

Another embodiment of the device is a wearable lower limb device that includes a distal module wearable by an individual that spans a distal skeletal joint and a proximal module wearable by the individual that spans a proximal skeletal joint, wherein the distal module and the proximal module are coupled. At least one of the distal and proximal modules includes a distal member wearable by the individual distal to the respective skeletal joint, a proximal member wearable by the individual proximal to the respective skeletal joint, and a link between the distal and proximal members, whereby actuation of the link will be translated to a force at the distal or proximal member that is normal to a major longitudinal axis extending through the distal and proximal members. In this embodiment, optionally, at least one of the other of the distal member and proximal member includes a crossing member, and the link extends from the crossing member of the distal member or the proximal member to the other of the distal member or the proximal member. In one specific embodiment, both the distal module and the proximal module include a distal member, a proximal member, a crossing member and a link. The distal module and the proximal module can be coupled by a common member, wherein the proximal member of the distal module is also at least a component of the distal member of the proximal module. The distal module and the proximal module can be rigidly coupled. In one embodiment, the common member includes a degree of freedom coupling the distal module to the proximal module. For example, the degree of freedom can be a hinge causing rotation in a plane essentially parallel to a plane of rotation of at least one of the proximal module and distal module. The distal module can be, for example, an exoskeleton, orthosis or prosthesis configured for use with a human knee joint, while the proximal module can be an exoskeleton, orthosis or prosthesis configured for use with a human hip joint. In a specific embodiment, the link of the distal and proximal modules can each include a winch actuator or a ballscrew actuator. In one particular preferred embodiment, the crossing member of the distal module includes a pulley and a cord linking the pulley, and a link of the distal module includes a winch actuator, whereby actuation of the link of the distal module causes extension of the human knee secured to the distal module. The distal member of the distal module can include, for example, a leaf spring linking the pulley to the distal member of the display module. In one embodiment, the crossing member of the distal module extends proximally from the hinge of the distal member of the proximal module. The link of the proximal module can include a cord and a winch actuator that is at the proximal member of the proximal module, wherein the cord extends from the crossing member of the proximal module to the winch actuator, whereby actuation of the link of the proximal module will cause flexion movement of a human hip secured to the proximal module. In an alternate embodiment, the link of the proximal module includes a ball screw actuator, whereby actuation of the link is bidirectional and, selectively causes flexion and extension of a human hip secured to the proximal member.

In another embodiment, the lower limb device further includes an ankle module that is distal to the distal module, wherein the ankle module is coupled to the distal module, and wherein the distal module and the ankle module share a common member. In one embodiment of this example, the ankle module includes an ankle distal member, an ankle proximal member, and an ankle link between the ankle distal number and the ankle proximal member, whereby actuation of the ankle link will be translated to a force at the ankle distal member or the ankle proximal member that is normal to a major longitudinal axis extending through the ankle distal end ankle proximal members. In one such embodiment of the lower limb device, at least one or the other of the ankle distal and the ankle proximal member includes an ankle crossing member, wherein the ankle link extends from the ankle crossing member of the ankle distal member or the ankle proximal member to the other of the ankle distal member or the ankle proximal member.

In one embodiment the crossing member of the ankle module extends proximally from the distal member of the ankle module. In a particular embodiment, the link of the ankle module includes a winch actuator at the proximal member of the ankle module, wherein a cord of the winch actuator extends from a proximal end of the crossing member to the winch actuator of the ankle module, whereby actuation of the link causes plantar flexion of human ankle secured to the ankle module.

The lower limb device of the invention can be, for example, an exoskeleton, orthosis or prosthesis for a human ankle, and the proximal module can be an exoskeleton, orthosis or prosthesis for a human knee.

Figure 21:
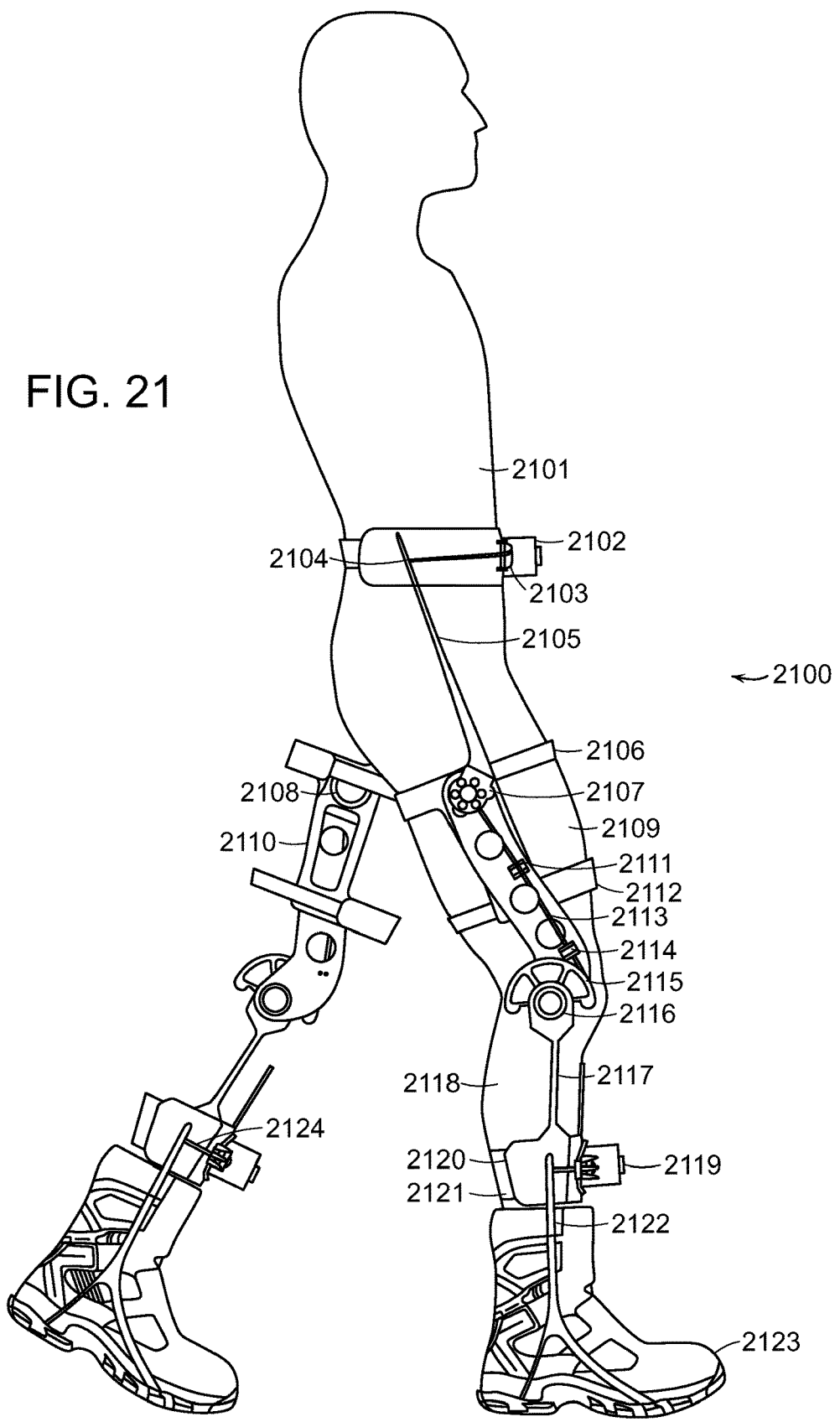
FIG. 21 is a side view of one embodiment of a lower limb exoskeleton of the invention.
Figure 22:
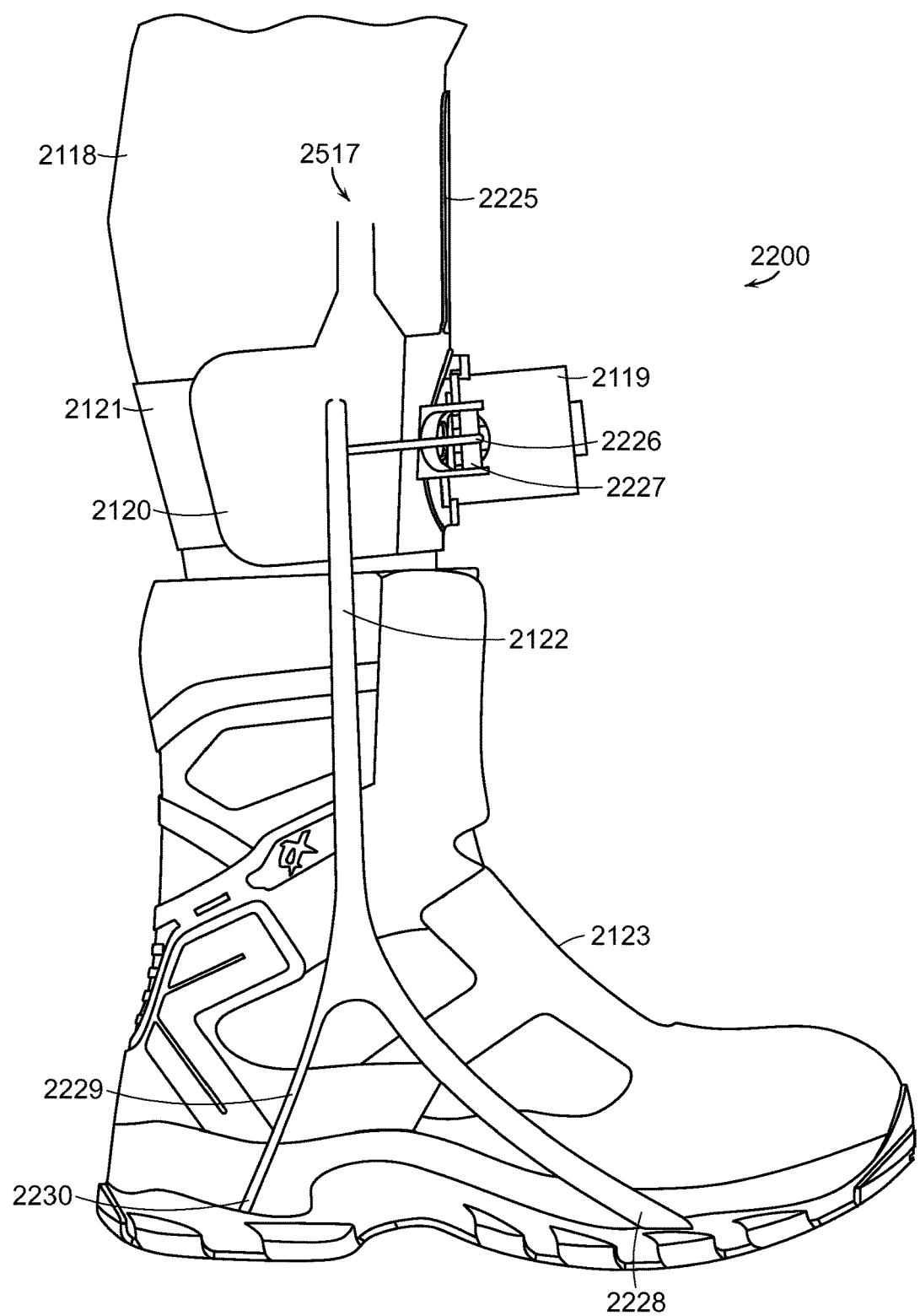
FIG. 22 is a side view of an ankle module of the lower limb exoskeleton of FIG. 21.

In yet another embodiment of the invention, lower limb exoskeleton 2100 (FIG. 21) includes modular sections that attach to an individual's waist 2101, thigh 2109, shank 2118, and foot 2123. Exoskeleton 2100 includes unidirectional winch actuators 2102, 2107 and 2119, to apply moments about the individual's hip, knee and ankle joints respectively. Exoskeleton 2100 applies a plantar-flexion moment about the individual's ankle, an extension moment about the knee, and a flexion moment about the hip. The unidirectional winch actuators apply mechanical power to the individual, while also permitting the individual completely transparent control. Exoskeleton 2100 can also apply zero torque to the individual by providing excess slack in cords, 2104, 2113, 2124, and 2126 (FIGS. 21-22). Additionally, winch actuators 2105, 2107 and 2119 preserve joint flexibility and do not constrain the hip, knee or ankle joints to planar motion, respectively. Flexible levers 2122, 2117 and 2105 which are built into exoskeleton 2100 are employed as series elastic elements to increase actuator shock tolerance, electrical energy efficiency, and peak exoskeleton power. The joint-specific design of exoskeleton 2100 results in a selectively low mass device that can apply substantial amounts of power to the individual.

As can be seen in FIG. 22, ankle portion 2200 of exoskeleton 2100 includes boot attachment 2202 and shank-mounted winch actuator 2119. Ankle module 2200 of the exoskeleton provides plantar-flexion moment about the ankle joint by actuating flexible levers attached to the boot. Elastic lever arm 2122 is integrated into boot 2202 by connection points at both the toe 2228 and heel 2230. Since exoskeleton 2100 only applies plantar-flexion moments, the connection between the heel and lever arm 2229 can be slender and lightweight. Boot attachment 2202 can be made of a variety of materials including, for example, carbon fiber and fiberglass composites. The flexibility of lever arm 2229 and winch actuation also maintains the ability of the individual's ankle to perform biological eversion and inversion movements. Anteriorly mounted winch actuator, 2119 is connected to a lightweight shin guard 2120, which is secured to the individual's calf with lightweight strap 2221. Shin mount 2225 extends from shin guard 2520 and serves to dissipate force.

Figure 23:
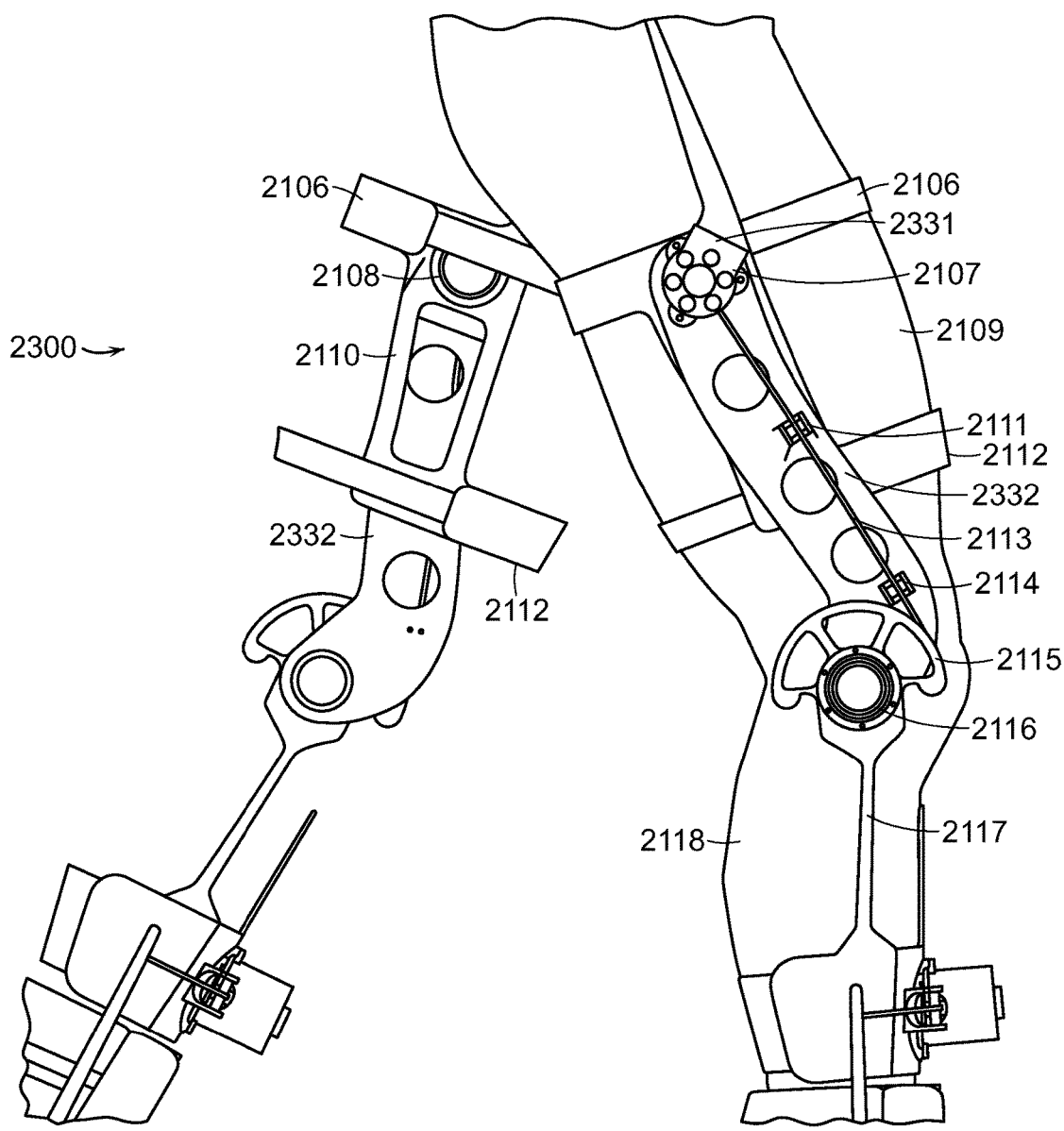
FIG. 23 is a side view of a knee module of the lower limb exoskeleton of FIG. 21.

Knee module 2300, shown in FIG. 23, includes large diameter pulley 2115 to apply an extension moment about the knee joint while maintaining a full range of motion. Knee exoskeleton 2300 utilizes large pulley 2115 to apply an extension moment about the knee while maintaining full knee range of motion. Knee actuator mount 2392 is connected to thigh cuff 2110 via rotary bearing 2108 to reduce knee constraints. Minimal shear and joint flexibility is achieved by including a bearing 2108 between knee actuator mount 2332 and thigh cuff 2110. Knee actuator mount 2332 houses knee winch actuator 2107, knee actuator electronics 2331, and upper and lower cord guides 2111 and 2114, respectively. Knee actuator mount 2332 is connected to the shank leaf spring 2117 via rotary bearing 2116. Additional rotary bearing 2108 minimizes the constraint on the knee joint imposed by knee bearing 2116. A linear bearing could also be used instead of rotary bearing 2108. Optionally, rotary bearing could be placed between flexible lever 2117 and shin guard 2120. Thigh cuff 2110 is secured to the body with lightweight straps 2106, 2112.

Figure 24:
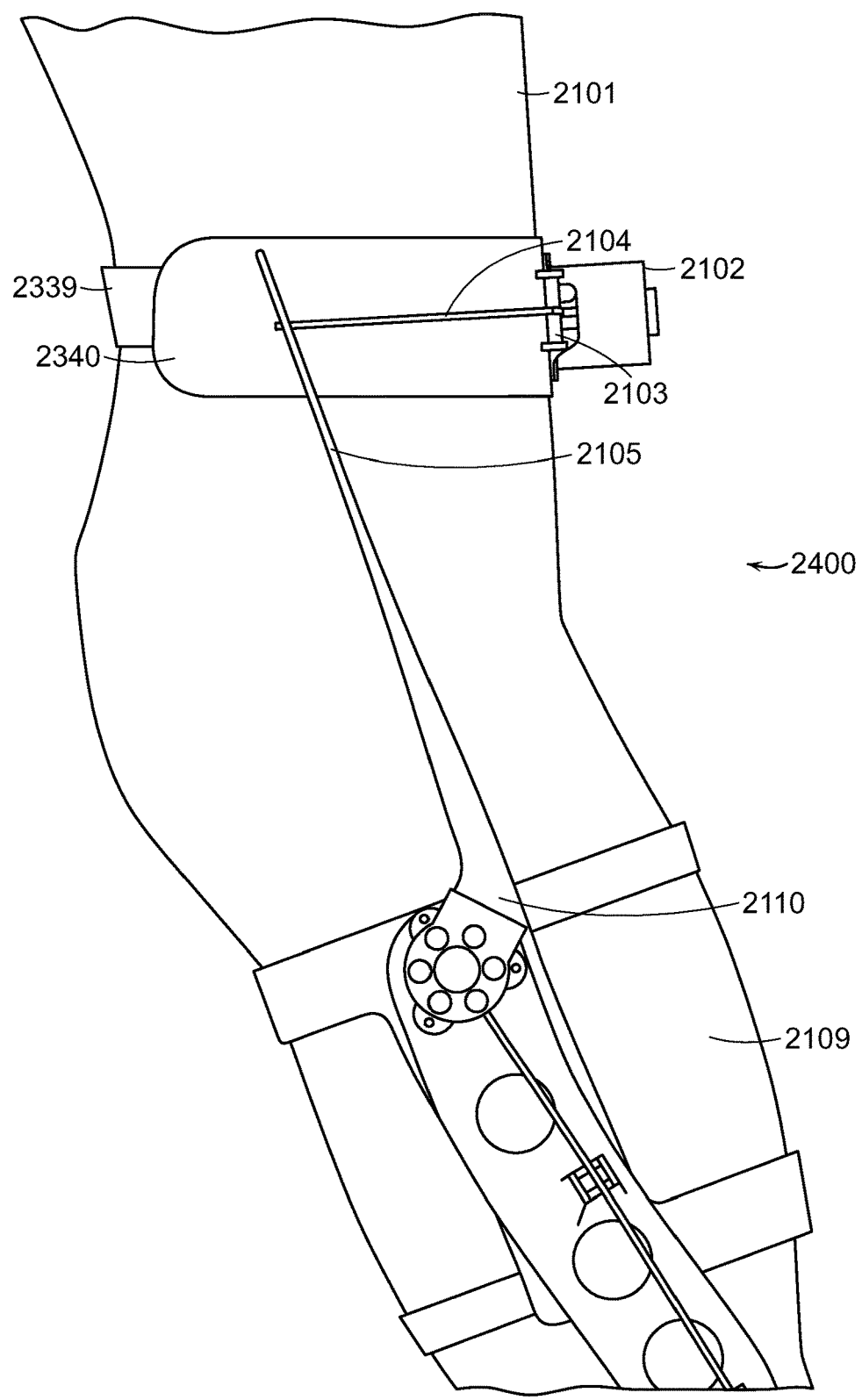
FIG. 24 is a side view of a hip module of the lower limb exoskeleton of FIG. 21.

As shown in FIG. 24, hip exoskeleton module 2400 employs elastic lever 2105 to store energy in the sagittal plane of the individual while allowing hip adduction/abduction and rotation. Similar to ankle exoskeleton 2200, hip exoskeleton 2400 employs an extended thigh lever arm 2105 to provide a geometric transmission to hip actuator 2102. Hip actuator 2102 routes cord 2104 around idler roller 2103 and is connected to thigh extension lever 2105. Hip actuator 2400 is attached to waist mount 2340 that is secured to the individual with strap 2339. The geometry of thigh extension lever 2105 allows for both hip flexibility and actuation.

Figure 25:
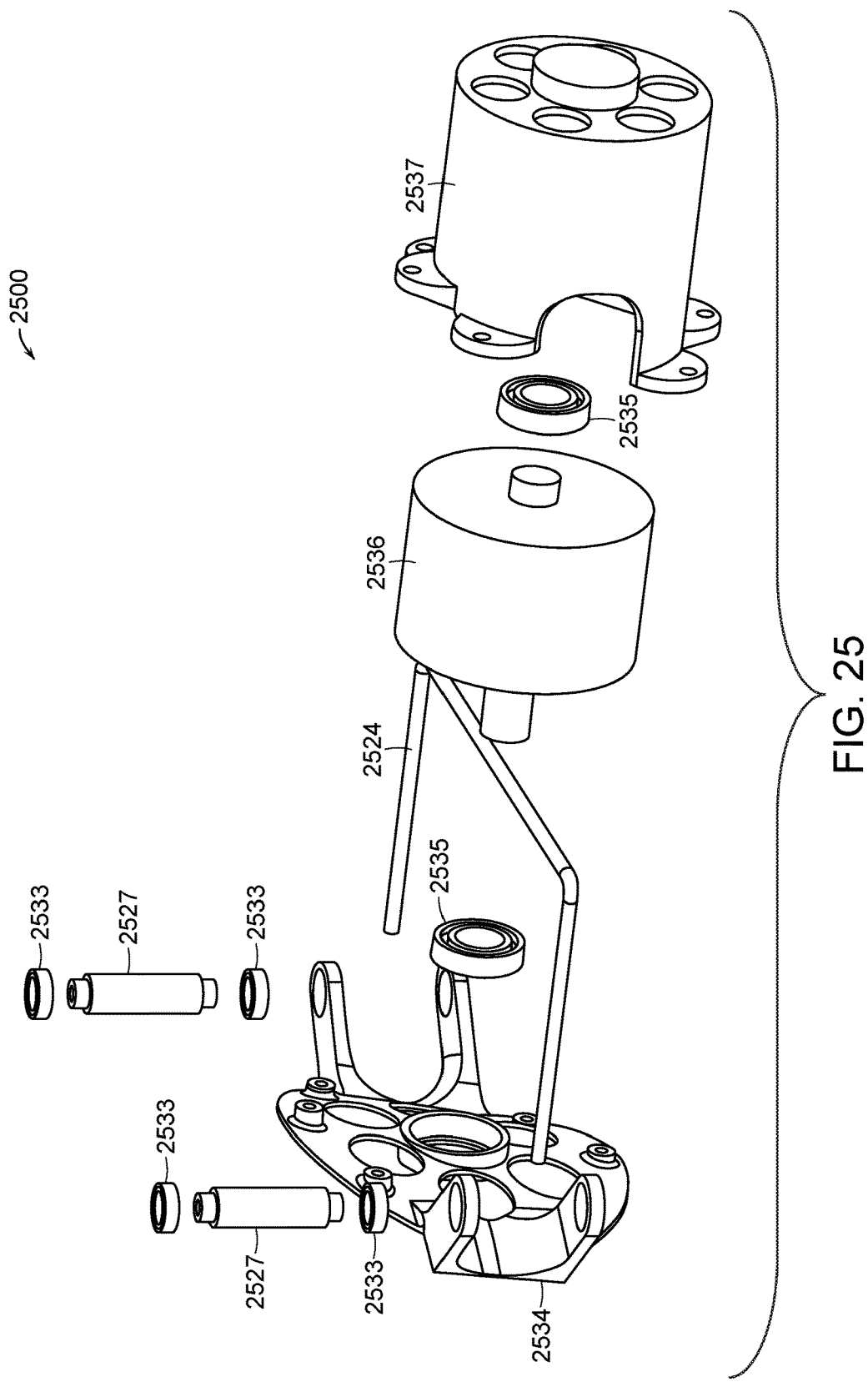
FIG. 25 is an exploded view of winch actuator of the lower limb exoskeleton of FIG. 21.

A suitable hip actuator can be, for example, winch actuator 2500, shown in FIG. 25, which employs high torque electric motors to efficiently and quietly actuate the joints. Winch actuator 2500 allows the exoskeleton to apply large amounts of the power to the individual wearer during certain portions of gait, and then apply zero torque during other portions of gait, which is a convenient feature for control. A conventional radial flux brushless motor or an axial flux brushless motor, for example, can be employed to actuate the exoskeleton module. Motor 2536, supported by rotational bearings 2535, wraps cord 2524 around an integrated spool. Motor cap 2537 houses the electromagnetics of motor 2536 and attaches motor 2538 to the actuator body 2534. Cord 2524 is routed around idler rollers 2527, supported by bearings 2533.

Figure 26B:
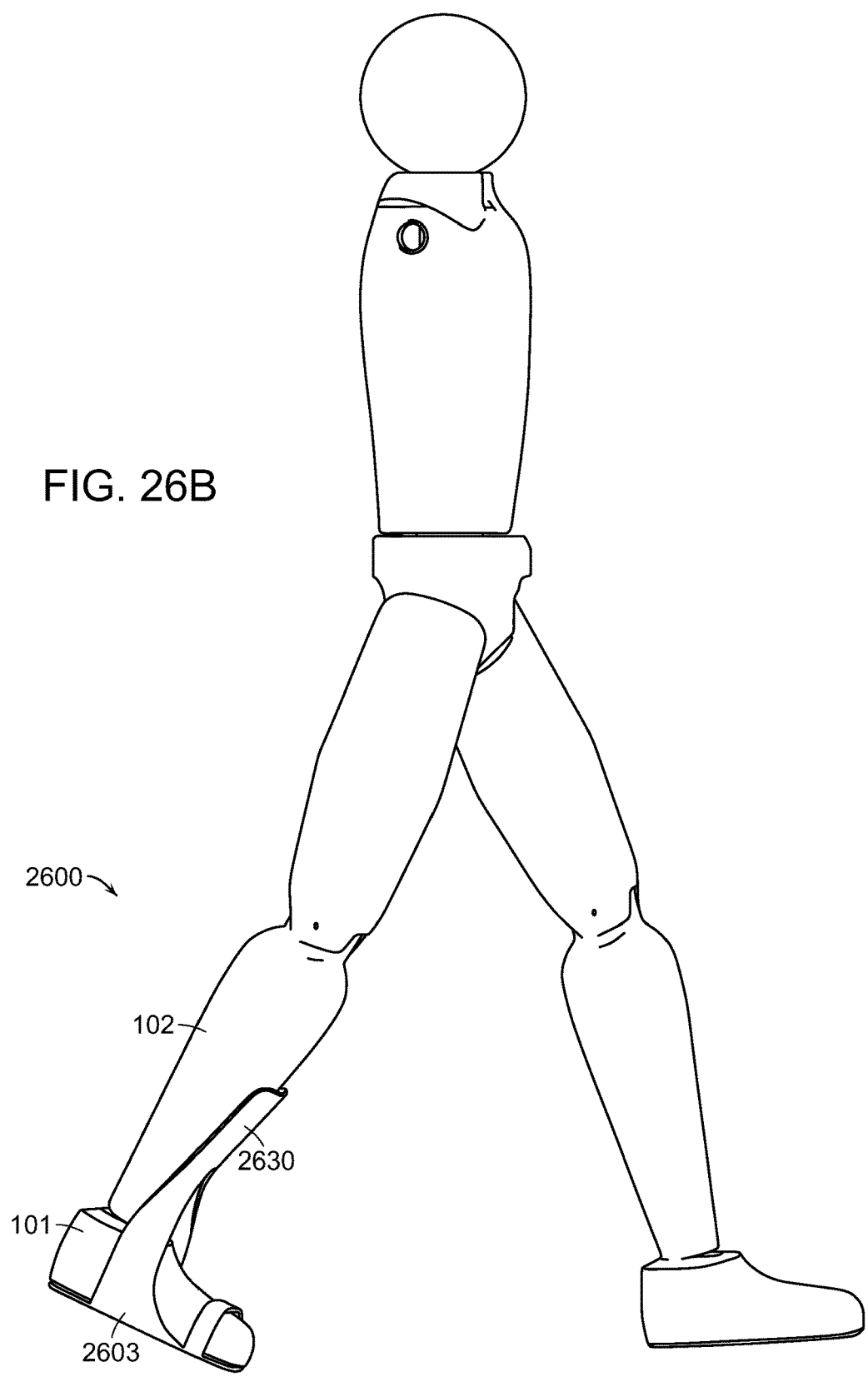
FIG. 26B is another perspective view of the embodiment of FIG. 26A, illustrating dorsiflexion.

An embodiment of a device of the invention that includes an ankle exoskeleton with a pneumatic actuator is illustrated in FIGS. 26A and 26B. Ankle exoskeleton 2600 has distal member 2603 connected to foot 101, and a proximal member 2604 attached to shank 102. Proximal shank member 2604 on ankle exoskeleton 2600 does not pass through a virtual horizontal plane of the ankle joint, such as virtual horizontal plane A illustrated in FIGS. 2A-2B. Distal foot component 2603 includes crossing member 2630 which is linked to proximal member 2604 via inflatable bladder actuator 2605. Force exerted by inflatable bladder actuator 2605 can be measured with a force sensor placed between actuator 2605 and proximal shank member 2604, similar to force sensor 111 described with reference to FIG. 3. Inflation of the bladder actuator 2605 causes plantar flexion of the ankle joint, as illustrated in FIG. 26A. Deflation of bladder actuator 2605 allows for dorsiflexion of the ankle joint, as illustrated in FIG. 26B. Valves (not shown) can be employed to effect inflation and deflation of bladder actuator 2605. The valves can be actuated by a controller, such as controller 107 described with respect to FIG. 1. An energy source to drive bladder actuator 2605 can be directly attached to proximal member 2604, distal member 2603, or a separate location, such as backpack or waist pack 106, as shown in FIG. 1.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A wearable device, comprising:
   a) a distal member wearable by an individual distal to a skeletal joint of the individual;
   b) a proximal member wearable by the individual proximal to the joint, wherein one of the distal member and the proximal member includes a crossing member extending across the joint toward the other of the distal member and the proximal member along a major longitudinal axis extending through the distal and proximal members; and
   c) a link between the distal member and the proximal member, wherein the link extends from the crossing member of the distal member or the proximal member, to the other of the distal member or the proximal member, and whereby actuation of the link will be translated to a force between the crossing member and the other of the distal member or proximal member that is substantially normal to the major longitudinal axis extending through the distal and proximal members within a range of relative movement between the crossing member and the other of the distal member and proximal member.

2. The device of claim 1, wherein the crossing member is rigid.

3. The device of claim 2, wherein the crossing member is not rigidly fixed to one or the other of the distal member and the proximal member.

4. The device of claim 1, wherein the crossing member is rigidly fixed to the one or the other of the distal member and the proximal member.

5. The device of claim 4, wherein the link includes a ball screw actuator.

6. The device of claim 4, wherein the link and crossing member are components of a series elastic actuator.

7. The device of claim 6, wherein the series elastic actuator is a bidirectional actuator.

8. The device of claim 7, wherein the bidirectional actuator is a pneumatic actuator.

9. The device of claim 8, wherein the pneumatic actuator includes a hardening series elastic element.

10. The device of claim 8, wherein the pneumatic actuator includes an inflatable bladder.

11. The device of claim 6, wherein the series elastic actuator is a unidirectional actuator.

12. The device of claim 11, wherein the unidirectional actuator is a pneumatic actuator.

13. The device of claim 11, wherein the unidirectional actuator is an electric spool actuator.

14. The device of claim 13, wherein the crossing member includes a distal end and a proximal end, wherein the distal end is fixed to the distal member at one end and is essentially normal to a major longitudinal axis of the distal member, and wherein the link extends between the proximal end of the crossing member and the proximal member.

15. The device of claim 14, wherein the distal member includes a surface that is essentially parallel to a plane that is normal to the major longitudinal axis extending between the distal and proximal members.

16. The device of claim 15, further including a second crossing member extending from the distal member, wherein the crossing members are essentially parallel to each other.

17. The device of claim 16, wherein the distal member is configured to support and to be secured to a human foot, the crossing members being configured to extend essentially dorsally and parallel to a tibia extending from the human foot, and wherein the proximal member is secured to the human calf, the electric spool actuator including a cable that is linked to the proximal end of the crossing member and spans the calf normally to a major longitudinal axis of the human tibia, whereby actuation of the actuator causes rotation of the distal member about the human ankle joint to thereby at least assist plantar flexion of the human foot while walking.

18. The device of claim 1, wherein the crossing member is not rigid.

19. The device of claim 18, wherein the link includes a strut, the strut extending from the proximal member to the distal member, whereby the crossing member and the strut span the axis about which the distal member rotates.

20. The device of claim 19, wherein the strut is constrained at the proximal member normally and laterally to a major longitudinal axis of the crossing member extending from the proximal member to the distal member, wherein the strut is not restricted along the major longitudinal axis of the crossing member.

21. The device of claim 20, wherein the link further includes at least one roller at the proximal member that constrains the strut normally and laterally.

22. The device of claim 21, wherein the link includes at least one pair of rollers in opposition to each other, wherein the strut is normally constrained between the pair of rollers.

23. The device of claim 22, wherein strut is curved at the pair of rollers, whereby shear force between the strut and the pair of rollers during rotation of the distal member about the axis spanned by the crossing member and the strut is less than it would be if the strut were straight at the pair of rollers.

24. The device of claim 23, wherein the strut includes a guide tube at the pair of rollers, wherein the crossing member extends through the guide tube.

25. The device of claim 24, including a pair of crossing members and a pair of struts.

26. The device of claim 25, wherein the struts are essentially straight between the rollers and the distal member.

27. The device of claim 26, wherein at least one of the struts deflects during eversion and inversion of a human foot secured to the distal member and a human calf secured to the proximal member.

28. The device of claim 27, wherein the struts are rigid.

29. The device of claim 25, wherein the struts are curved, whereby the struts operate as series springs during a normal walking cycle of a human foot secured to the distal member and a human calf secured to the proximal member.

30. The device of claim 25, wherein the link further includes a winch actuator assembly attached to a proximal end of the pair of crossing members, whereby actuation of the link will cause retraction of the crossing members, which causes rotation of the distal member and plantar flexion of a human foot secured to the distal member about a human ankle joint.

31. The device of claim 25, wherein the pair of crossing members is fixed to a proximal end of the distal member.

32. The device of claim 31, further including a second pair of crossing members fixed to a distal end of the distal member.

33. The device of claim 32, wherein the link further includes a second winch actuator assembly attached to a proximal end of the second pair of crossing members, whereby selective actuation of the link causes retraction of the second pair of crossing members, which causes rotation of the distal member and dorsiflexion of a human foot secured to the distal member about the human ankle joint.

34. The device of claim 1, wherein the distal member is configured to fit a human calf.

35. The device of claim 34, wherein the proximal member is configured to fit a human thigh.

36. The device of claim 35, wherein the crossing member extends proximally from the distal member, and the link extends between the proximal member and a proximal end of the crossing member, whereby actuation of the link will cause extension of a human leg secured to the proximal and distal members.

37. The device of claim 35, wherein the crossing member extends distally from the proximal member, and the link extends between a distal end of the crossing member and the distal member, whereby actuation of the link will cause extension of a human leg secured to the proximal and distal members.

38. The device of claim 1, wherein the proximal member is configured to fit a human waist.

39. The device of claim 38, wherein the distal member is configured to fit a human thigh.

40. The device of claim 39, wherein the crossing member extends proximally from the distal member.

41. The device of claim 40, wherein the link includes a bidirectional actuator, whereby actuation of the link will rotate the distal member and a human thigh secured to the distal member about a hip joint of a human wearing the device.

42. The device of claim 41, wherein the bidirectional actuator is a ball screw actuator.

43. A wearable lower limb device, comprising:
a) a distal module wearable by an individual that spans a distal skeletal joint; and
b) a proximal module wearable by the individual that spans a proximal skeletal joint,
wherein the distal module and the proximal module are coupled, and wherein at least one of the distal and proximal modules includes
  i) a distal member wearable by the individual distal to the respective skeletal joint;
  ii) a proximal member wearable by the individual proximal to the respective skeletal joint, wherein one of the distal member and the proximal member includes a crossing member extending across the joint toward the other of the distal member and the proximal member along a major longitudinal axis extending through the distal and proximal members; and
  iii) a link between the distal member and the proximal member, wherein the link extends from the crossing member of the distal member or the proximal member, to the other of the distal member or the proximal member, and whereby actuation of the link will be translated to a force between the crossing member and the other of the distal member or proximal member that is substantially normal to the major longitudinal axis extending through the distal and proximal members within a range of relative movement between the crossing member and the other of the distal member and proximal member.

44. The lower limb device of claim 43, wherein the distal module is configured for use with a human ankle, and the proximal module is configured for use with a human knee.

45. The lower limb device of claim 43, wherein both the distal module and the proximal module include a distal member, a proximal member, a crossing member and a link.

46. The lower limb device of claim 45, wherein the distal module and the proximal module are coupled by a common member, wherein the proximal member of the distal module is also at least a component of the distal member of the proximal module.

47. The lower limb device of claim 45, wherein the distal module and the proximal module are rigidly coupled.

48. The lower limb device of claim 46, wherein the common member further includes a degree of freedom coupling the distal module to the proximal module.

49. The lower limb device of claim 48, wherein the degree of freedom is a hinge causing rotation in a plane essentially parallel to a plane of rotation of at least one of the proximal module and the distal module.

50. The lower limb device of claim 49, wherein the distal module is a device configured for use with a human knee joint, and the proximal module is a device configured for use with a human hip joint.

51. The lower limb device of claim 50, wherein the links of the distal and proximal module each include a winch actuator or a ball screw actuator.

52. The lower limb device of claim 51, wherein the crossing member of the distal module includes a pulley and a cord linking the pulley, and a link of the distal module includes a winch actuator, whereby actuation of the link of the distal module causes extension of a human knee secured to the distal module.

53. The lower limb device of claim 52, wherein the distal member of the distal module includes a leaf spring linking the pulley to the distal member of the distal module.

54. The lower limb device of claim 53, wherein the crossing member of the proximal module extends proximally from the hinge of the distal member of the proximal module.

55. The lower limb device of claim 54, wherein the link of the proximal module includes a cord and a winch actuator that is at the proximal member of the proximal module, and wherein the cord extends from the crossing member of the proximal module to the winch actuator, whereby actuation of the link of the proximal module will cause flexion movement of a human hip secured to the proximal module.

56. The lower limb device of claim 54, wherein the link of the proximal module includes a ball screw actuator, whereby actuation of the link is bidirectional and selectively causes flexion and extension of a human hip secured to the proximal member.

57. The lower limb device of claim 52, further including an ankle module that is distal to the distal module, wherein the ankle module is coupled to the distal module, the distal module and the ankle module sharing a common member.

58. The lower limb device of claim 57, wherein the ankle module includes:
a) an ankle distal member;
b) an ankle proximal member; and
c) an ankle link between the ankle distal member and the ankle proximal member, whereby actuation of the link will be translated to a force at the ankle distal member or the ankle proximal member that is normal to a major longitudinal axis extending through the ankle distal and ankle proximal members.

59. The lower limb device of claim 58, wherein at least one or the other of the ankle distal member or ankle proximal member includes an ankle crossing member, and wherein the ankle link extends from the ankle crossing member of the ankle distal member or the ankle proximal member to the other of the ankle distal member or the ankle proximal member.

60. The lower limb device of claim 59, wherein the crossing member of the ankle module extends proximally from the distal member of the ankle module.

61. The lower limb device of claim 60, wherein the link of the ankle module includes a winch actuator at the proximal member of the ankle module, wherein a cord of the winch actuator extends from a proximal end of the crossing member to the winch actuator of the ankle module, whereby actuation of the link causes plantar flexion of a human ankle secured to the ankle module.

* * * * *